United States Patent
Defosset et al.

(10) Patent No.: US 11,937,864 B2
(45) Date of Patent: Mar. 26, 2024

(54) ABLATION SYSTEMS WITH PARAMETER-BASED MODULATION AND RELATED DEVICES AND METHODS

(71) Applicant: DFine, Inc., South Jordan, UT (US)

(72) Inventors: Joshua Defosset, Los Gatos, CA (US); Nate Shirley, Pleasant Grove, UT (US); Eric Wong, Sunnyvale, CA (US); Craig Purdy, Sunnyvale, CA (US); Oleg Yurchak, Milpitas, CA (US); Jimmy Chi-Yun Chan, San Mateo, CA (US); Robert D. Poser, Scotts Valley, CA (US)

(73) Assignee: DFine, Inc., South Jordan, UT (US)

( * ) Notice: Subject to any disclaimer, the term of this patent is extended or adjusted under 35 U.S.C. 154(b) by 378 days.

(21) Appl. No.: 16/677,124

(22) Filed: Nov. 7, 2019

(65) Prior Publication Data

US 2020/0146743 A1    May 14, 2020

Related U.S. Application Data

(60) Provisional application No. 62/757,596, filed on Nov. 8, 2018, provisional application No. 62/757,578, filed on Nov. 8, 2018.

(51) Int. Cl.
*A61B 18/12* (2006.01)
*A61B 17/00* (2006.01)
(Continued)

(52) U.S. Cl.
CPC .......... *A61B 18/14* (2013.01); *A61B 18/1206* (2013.01); *G06F 3/0482* (2013.01);
(Continued)

(58) Field of Classification Search
CPC ................ A61B 18/14; A61B 18/1206; A61B 2017/00212; A61B 2018/00339;
(Continued)

(56) References Cited

U.S. PATENT DOCUMENTS 2,688,329 A  9/1954 Wallace
3,140,623 A  7/1964 Hoose
(Continued)

FOREIGN PATENT DOCUMENTS

CA  2785207  7/2011
CN  88203061  11/1988
(Continued)

OTHER PUBLICATIONS

US 7,063,700 B2, 06/2006, Michelson (withdrawn)
(Continued)

*Primary Examiner* — Joseph A Stoklosa
*Assistant Examiner* — Annie L Shoulders
(74) *Attorney, Agent, or Firm* — Dorsey & Whitney LLP

(57) ABSTRACT

The invention relates to a magnetic-navigation joint type puncture needle which comprises a head section and needle sections, wherein, the head section is made of stainless steel material with high magnetic conductivity and is connected with the following needle sections coaxially mounted with the head section through a flexible joint; two needle sections are also coaxially connected with each other through a flexible joint; the needle sections are made of non-magnetic stainless steel material; the flexible joints adopts serpentine tubes formed by melting and engraving cobalt-chromium alloy through laser; and both the head section and the needle sections can be bent, but the flexibility of the head section and that of the needle sections are smaller than the flexibility of the flexible joints. According to the invention, an extra magnetic field force is used to cause the head section of the (Continued)

needle to deflect, so that the following purposes can be achieved that the insertion direction of the needle can be changed, and the other needle sections also deflect with the deflection of the head section; accurate navigation for and control over puncture path and puncture position when the puncture needle performs a non-direct channel puncture in a human body; the puncture needle provided by the invention can reach niduses which other types of puncture needles can not reach; the application scope of minimally invasive surgery is expanded; iatrogenic injuries can be reduced; and patients can be benefited.

18 Claims, 17 Drawing Sheets

(51) Int. Cl.
| | | |
|---|---|---|
| | *A61B 18/00* | (2006.01) |
| | *A61B 18/14* | (2006.01) |
| | *G06F 3/0482* | (2013.01) |
| | *G06F 3/0488* | (2022.01) |
| | *A61B 90/00* | (2016.01) |

(52) U.S. Cl.
CPC .. *G06F 3/0488* (2013.01); *A61B 2017/00115* (2013.01); *A61B 2017/00212* (2013.01); *A61B 2017/00393* (2013.01); *A61B 2018/00339* (2013.01); *A61B 2018/00577* (2013.01); *A61B 2018/0072* (2013.01); *A61B 2018/00821* (2013.01); *A61B 2018/00875* (2013.01); *A61B 2018/00916* (2013.01); *A61B 2090/376* (2016.02)

(58) Field of Classification Search
CPC .. A61B 2018/00577; A61B 2018/0072; A61B 2018/00821; A61B 2018/00875; G06F 3/0482; G06F 3/0488
See application file for complete search history.

(56) References Cited

U.S. PATENT DOCUMENTS

| | | |
|---|---|---|
| 3,228,400 A | 1/1966 | Armao |
| 3,503,385 A | 3/1970 | Stevens |
| 3,625,200 A | 12/1971 | Muller |
| 3,664,344 A | 5/1972 | Bryne |
| 3,794,039 A | 2/1974 | Kollner et al. |
| 3,908,637 A | 9/1975 | Doroshow |
| 4,033,331 A | 7/1977 | Guss et al. |
| 4,131,597 A | 12/1978 | Bluethgen et al. |
| 4,236,520 A | 12/1980 | Anderson |
| 4,276,880 A | 7/1981 | Malmin |
| 4,294,251 A | 10/1981 | Grennwald et al. |
| 4,337,773 A | 7/1982 | Raftopoulos et al. |
| 4,386,717 A | 6/1983 | Koob |
| 4,399,814 A | 8/1983 | Pratt, Jr. et al. |
| 4,411,266 A | 10/1983 | Cosman |
| 4,456,017 A | 6/1984 | Miles |
| 4,473,077 A | 9/1984 | Noiles |
| 4,476,861 A | 10/1984 | Dimakos et al. |
| 4,578,061 A | 3/1986 | Lemelson |
| 4,586,923 A | 5/1986 | Gould et al. |
| 4,595,006 A | 6/1986 | Burke et al. |
| 4,619,263 A | 10/1986 | Frisbie et al. |
| 4,627,434 A | 12/1986 | Murray |
| 4,641,654 A | 2/1987 | Samson et al. |
| 4,653,489 A | 3/1987 | Tronzo |
| 4,668,295 A | 5/1987 | Bajpai |
| 4,719,968 A | 1/1988 | Speros |
| 4,722,948 A | 2/1988 | Sanderson |
| 4,731,054 A | 3/1988 | Billeter et al. |
| 4,742,817 A | 5/1988 | Kawashima et al. |
| 4,747,840 A | 5/1988 | Ladika et al. |
| 4,748,969 A | 6/1988 | Wardle |
| 4,784,638 A | 11/1988 | Ghajar et al. |
| 4,795,602 A | 1/1989 | Pretchel et al. |
| 4,842,603 A | 6/1989 | Draenert |
| 4,843,112 A | 6/1989 | Gerhart et al. |
| 4,846,814 A | 7/1989 | Ruiz |
| 4,865,586 A | 9/1989 | Hedberg |
| 4,869,906 A | 9/1989 | Dingeldein et al. |
| 4,888,366 A | 12/1989 | Chu et al. |
| 4,900,303 A | 2/1990 | Lemelson |
| 4,961,730 A | 10/1990 | Bodicky et al. |
| 4,961,731 A | 10/1990 | Poncy |
| 4,963,151 A | 10/1990 | Ducheyene et al. |
| 4,969,870 A | 11/1990 | Kramer et al. |
| 4,969,888 A | 11/1990 | Scholten et al. |
| 4,982,730 A | 1/1991 | Royce |
| 4,998,923 A | 3/1991 | Samson et al. |
| 5,004,501 A | 4/1991 | Faccioli |
| 5,017,627 A | 5/1991 | Bonfield |
| 5,046,513 A | 9/1991 | O'Leary et al. |
| 5,049,137 A | 9/1991 | Thompson |
| 5,049,157 A | 9/1991 | Mittelmeier et al. |
| 5,059,193 A | 10/1991 | Kuslich |
| 5,085,861 A | 2/1992 | Gerhart et al. |
| 5,088,991 A | 2/1992 | Weldon |
| 5,116,305 A | 2/1992 | Milder et al. |
| 5,092,891 A | 3/1992 | Kummer et al. |
| 5,103,804 A | 4/1992 | Abele |
| 5,108,404 A | 4/1992 | Scholten et al. |
| 5,112,303 A | 5/1992 | Pudenz et al. |
| 5,114,414 A | 5/1992 | Buchbinder |
| 5,147,334 A | 9/1992 | Moss |
| 5,156,606 A | 10/1992 | Chin |
| 5,163,431 A | 11/1992 | Greip |
| 5,184,757 A | 2/1993 | Giannuzzi |
| 5,188,619 A | 2/1993 | Myers |
| 5,196,201 A | 3/1993 | Larsson et al. |
| 5,197,971 A | 3/1993 | Bonutti |
| 5,211,631 A | 5/1993 | Sheaff |
| 5,231,989 A | 8/1993 | Middleman et al. |
| 5,242,082 A | 9/1993 | Giannuzzi |
| 5,264,214 A | 11/1993 | Rhee et al. |
| 5,266,248 A | 11/1993 | Ohtsuka et al. |
| 5,269,750 A | 12/1993 | Grulke et al. |
| 5,282,821 A | 2/1994 | Donahue |
| 5,284,128 A | 2/1994 | Hart |
| 5,285,795 A | 2/1994 | Ryan et al. |
| 5,295,980 A | 3/1994 | Ersek |
| 5,296,026 A | 3/1994 | Monroe et al. |
| 5,308,342 A | 5/1994 | Sepetka et al. |
| 5,322,064 A | 6/1994 | Lundquist |
| 5,322,505 A | 6/1994 | Krause et al. |
| 5,334,181 A | 8/1994 | Rubinsky et al. |
| 5,336,699 A | 8/1994 | Cooke et al. |
| 5,343,877 A | 9/1994 | Park |
| 5,352,715 A | 10/1994 | Wallace et al. |
| 5,356,629 A | 10/1994 | Sander |
| 5,360,416 A | 11/1994 | Ausherman et al. |
| 5,368,598 A | 11/1994 | Hasson |
| 5,372,587 A | 12/1994 | Hammerslag et al. |
| 5,378,234 A | 1/1995 | Hammerslag et al. |
| 5,380,307 A | 1/1995 | Chee et al. |
| 5,385,563 A | 1/1995 | Gross |
| 5,389,073 A | 2/1995 | Imran |
| 5,425,770 A | 6/1995 | Piez et al. |
| 5,431,168 A | 7/1995 | Webster, Jr. |
| 5,431,639 A | 7/1995 | Shaw |
| 5,437,636 A | 8/1995 | Snoke et al. |
| 5,449,301 A | 9/1995 | Hanna et al. |
| 5,449,351 A | 9/1995 | Zohmann |
| 5,458,597 A | 10/1995 | Edwards et al. |
| 5,480,382 A | 1/1996 | Hammerslag et al. |
| 5,484,424 A | 1/1996 | Cottenceau et al. |
| 5,489,275 A | 2/1996 | Thompson et al. |
| 5,496,330 A | 3/1996 | Bates et al. |
| 5,512,610 A | 4/1996 | Lin |
| 5,514,130 A | 5/1996 | Baker |
| 5,514,137 A | 5/1996 | Coutts |

(56) References Cited

U.S. PATENT DOCUMENTS

| | | |
|---|---|---|
| 5,531,715 A | 7/1996 | Engelson et al. |
| 5,535,922 A | 7/1996 | Maziarz |
| 5,549,542 A | 8/1996 | Kovalcheck |
| 5,549,637 A | 8/1996 | Crainich |
| 5,549,679 A | 8/1996 | Kuslich |
| 5,554,114 A | 9/1996 | Wallace et al. |
| 5,571,085 A | 11/1996 | Accisano, III |
| 5,571,088 A | 11/1996 | Lennox |
| 5,574,075 A | 11/1996 | Draemert |
| 5,599,346 A | 2/1997 | Edwards et al. |
| 5,616,121 A | 4/1997 | McKay |
| 5,620,447 A | 4/1997 | Smith et al. |
| 5,620,467 A | 4/1997 | Wagner |
| 5,624,396 A | 4/1997 | McNamara et al. |
| 5,628,771 A | 5/1997 | Mizukawa et al. |
| 5,637,090 A | 6/1997 | McGee |
| 5,637,091 A | 6/1997 | Hakky et al. |
| 5,662,680 A | 9/1997 | Desai |
| 5,681,282 A | 10/1997 | Eggers et al. |
| 5,681,289 A | 10/1997 | Wilcox et al. |
| 5,681,317 A | 10/1997 | Caldarise |
| 5,685,826 A | 11/1997 | Bonutti |
| 5,695,513 A | 12/1997 | Johnson et al. |
| 5,697,536 A | 12/1997 | Eggers et al. |
| 5,697,909 A | 12/1997 | Eggers et al. |
| 5,700,157 A | 12/1997 | Chung |
| 5,704,926 A | 1/1998 | Sutton |
| 5,709,697 A | 1/1998 | Ratcliff et al. |
| 5,725,568 A | 3/1998 | Hastings |
| 5,735,829 A | 4/1998 | Cherian |
| 5,741,320 A | 4/1998 | Thornton et al. |
| 5,766,153 A | 6/1998 | Eggers et al. |
| 5,800,408 A | 9/1998 | Strauss et al. |
| 5,810,804 A | 9/1998 | Gough |
| 5,810,867 A | 9/1998 | Zarbateny et al. |
| 5,820,592 A | 10/1998 | Hammerslag et al. |
| 5,833,632 A | 11/1998 | Jacobsen et al. |
| 5,833,692 A | 11/1998 | Cesarini et al. |
| 5,847,046 A | 12/1998 | Jiang et al. |
| 5,849,028 A | 12/1998 | Chen |
| 5,851,212 A | 12/1998 | Zirps et al. |
| 5,855,577 A | 1/1999 | Murphy-Chutorian et al. |
| 5,858,003 A | 1/1999 | Atala |
| 5,860,952 A | 1/1999 | Quinn |
| 5,860,974 A | 1/1999 | Abele |
| 5,876,373 A | 3/1999 | Giba et al. |
| 5,891,027 A | 4/1999 | Tu |
| 5,902,251 A | 5/1999 | Vanhooydonk |
| 5,902,839 A | 5/1999 | Lautenschlager et al. |
| 5,914,356 A | 6/1999 | Erbe |
| 5,921,956 A | 7/1999 | Grinberg et al. |
| 5,928,239 A | 7/1999 | Mirza |
| 5,931,829 A | 8/1999 | Burbank et al. |
| 5,944,715 A | 8/1999 | Goble et al. |
| 5,947,964 A | 9/1999 | Eggers |
| 5,972,015 A | 10/1999 | Scribner et al. |
| 5,997,581 A | 12/1999 | Khalili |
| 6,019,765 A | 2/2000 | Thornhill et al. |
| 6,027,487 A | 2/2000 | Crocker |
| 6,030,360 A | 2/2000 | Biggs |
| 6,048,346 A | 4/2000 | Reiley et al. |
| 6,059,739 A | 5/2000 | Baumann |
| 6,063,078 A | 5/2000 | Wittkampf |
| 6,064,902 A | 5/2000 | Haissaguerre |
| 6,066,154 A | 5/2000 | Reiley et al. |
| 6,066,176 A | 5/2000 | Oshida |
| 6,073,051 A | 6/2000 | Sharkey et al. |
| 6,080,801 A | 6/2000 | Draenert et al. |
| 6,099,514 A | 8/2000 | Sharkey et al. |
| 6,106,524 A | 8/2000 | Eggers et al. |
| 6,106,539 A | 8/2000 | Fortier |
| 6,110,155 A | 8/2000 | Baudino |
| 6,123,702 A | 9/2000 | Swanson |
| 6,127,597 A | 10/2000 | Beyar et al. |
| 6,135,999 A | 10/2000 | Fanton et al. |
| 6,146,355 A | 11/2000 | Biggs |
| 6,156,254 A | 12/2000 | Andrews et al. |
| 6,183,435 B1 | 2/2001 | Bumbalough et al. |
| 6,203,507 B1 | 3/2001 | Wadsworth et al. |
| 6,203,574 B1 | 3/2001 | Kawamura |
| 6,228,052 B1 | 5/2001 | Pohndorf |
| 6,228,904 B1 | 5/2001 | Yadav et al. |
| 6,231,569 B1 | 5/2001 | Bek et al. |
| 6,231,615 B1 | 5/2001 | Preissman |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,251,092 B1 | 6/2001 | Qin et al. |
| 6,258,086 B1 | 7/2001 | Ashley et al. |
| 6,270,476 B1 | 8/2001 | Santoianni et al. |
| 6,280,413 B1 | 8/2001 | Clark et al. |
| 6,280,434 B1 | 8/2001 | Kinoshita et al. |
| 6,280,441 B1 | 8/2001 | Ryan |
| 6,280,456 B1 | 8/2001 | Scribner et al. |
| 6,280,473 B1 | 8/2001 | Lemperle et al. |
| 6,283,960 B1 | 9/2001 | Ashley |
| 6,291,547 B1 | 9/2001 | Lyles |
| 6,312,428 B1 | 11/2001 | Eggers |
| 6,312,454 B1 | 11/2001 | Stockel et al. |
| 6,332,894 B1 | 12/2001 | Stalcup et al. |
| 6,348,055 B1 | 2/2002 | Preissman |
| 6,352,533 B1 | 3/2002 | Ellman et al. |
| 6,358,251 B1 | 3/2002 | Mirza |
| 6,375,659 B1 | 4/2002 | Erbe et al. |
| 6,383,188 B2 | 5/2002 | Kuslich et al. |
| 6,383,190 B1 | 5/2002 | Preissman |
| 6,395,007 B1 | 5/2002 | Bhatnagar et al. |
| 6,408,889 B1 | 6/2002 | Komachi |
| 6,409,722 B1 * | 6/2002 | Hoey .................. A61B 18/18 606/41 |
| 6,428,894 B1 | 8/2002 | Babich et al. |
| 6,437,019 B1 | 8/2002 | Rusin et al. |
| 6,440,138 B1 | 8/2002 | Reiley et al. |
| 6,447,506 B1 | 9/2002 | Swanson et al. |
| 6,447,514 B1 | 9/2002 | Stalcup et al. |
| 6,464,683 B1 | 10/2002 | Samuelson et al. |
| 6,478,793 B1 | 11/2002 | Cosman et al. |
| 6,479,565 B1 | 11/2002 | Stanley |
| 6,484,904 B1 | 11/2002 | Horner et al. |
| 6,506,217 B1 | 1/2003 | Arnett |
| 6,511,471 B2 | 1/2003 | Rosenman et al. |
| 6,524,296 B1 | 2/2003 | Beals |
| 6,565,588 B1 | 5/2003 | Clement et al. |
| 6,575,969 B1 | 6/2003 | Rittman et al. |
| 6,575,978 B2 | 6/2003 | Peterson et al. |
| 6,576,249 B1 | 6/2003 | Gendler et al. |
| 6,582,446 B1 | 6/2003 | Marchosky |
| 6,592,559 B1 | 7/2003 | Pakter et al. |
| 6,599,961 B1 | 7/2003 | Pienkowski et al. |
| 6,602,248 B1 | 8/2003 | Sharps et al. |
| 6,607,544 B1 | 8/2003 | Boucher et al. |
| 6,613,054 B2 | 9/2003 | Scribner et al. |
| 6,620,162 B2 | 9/2003 | Kuslich et al. |
| 6,622,731 B2 | 9/2003 | Daniel et al. |
| 6,623,448 B2 | 9/2003 | Slater |
| 6,638,268 B2 | 10/2003 | Naizi |
| 6,663,647 B2 | 10/2003 | Reiley et al. |
| 6,641,587 B2 | 11/2003 | Scribner et al. |
| 6,645,213 B2 | 11/2003 | Sand et al. |
| 6,676,665 B2 | 1/2004 | Foley et al. |
| 6,679,886 B2 | 1/2004 | Weikel et al. |
| 6,689,823 B1 | 2/2004 | Bellare et al. |
| 6,692,532 B1 | 2/2004 | Healy et al. |
| 6,716,216 B1 | 4/2004 | Boucher et al. |
| 6,719,761 B1 | 4/2004 | Reiley et al. |
| 6,719,773 B1 | 4/2004 | Boucher et al. |
| 6,726,691 B2 | 4/2004 | Osorio et al. |
| 6,730,095 B2 | 5/2004 | Olson, Jr. et al. |
| 6,740,090 B1 | 5/2004 | Cragg et al. |
| 6,740,093 B2 | 5/2004 | Hochschuler et al. |
| 6,743,239 B1 | 6/2004 | Kuehn et al. |
| 6,746,451 B2 | 6/2004 | Middleton et al. |
| 6,752,863 B2 | 6/2004 | Lyles et al. |
| 6,753,007 B2 | 6/2004 | Haggard et al. |

(56) References Cited

U.S. PATENT DOCUMENTS

| | | |
|---|---|---|
| 6,770,079 B2 | 8/2004 | Bhatnagar et al. |
| 6,814,734 B2 | 11/2004 | Chappuis et al. |
| 6,814,736 B2 | 11/2004 | Reiley et al. |
| 6,818,001 B2 | 11/2004 | Wulfman et al. |
| 6,832,984 B2 | 12/2004 | Stelzer et al. |
| 6,835,193 B2 | 12/2004 | Epstein et al. |
| 6,837,867 B2 | 1/2005 | Kortelling |
| 6,863,672 B2 | 3/2005 | Reiley et al. |
| 6,869,430 B2 | 3/2005 | Balbierz et al. |
| 6,869,445 B1 | 3/2005 | Johnson |
| 6,875,219 B2 | 4/2005 | Arramon |
| 6,881,214 B2 | 4/2005 | Cosman et al. |
| 6,887,246 B2 | 5/2005 | Bhatnagar et al. |
| 6,899,715 B1 | 5/2005 | Beaty |
| 6,899,719 B2 | 5/2005 | Reiley et al. |
| 6,907,884 B2 | 6/2005 | Pellegrino et al. |
| 6,913,594 B2 | 7/2005 | Coleman et al. |
| 6,916,306 B1 | 7/2005 | Jenkins et al. |
| 6,923,813 B2 | 8/2005 | Phillips |
| 6,945,956 B2 | 9/2005 | Waldhauser et al. |
| 6,953,594 B2 | 10/2005 | Lee et al. |
| 6,955,716 B2 | 10/2005 | Xu et al. |
| 6,976,987 B2 | 12/2005 | Flores |
| 6,979,312 B2 | 12/2005 | Shimada |
| 6,979,352 B2 | 12/2005 | Reynolds |
| 6,981,981 B2 | 1/2006 | Reiley et al. |
| 6,991,616 B2 | 1/2006 | Bencini et al. |
| 6,998,128 B2 | 2/2006 | Haggard et al. |
| 7,004,930 B2 | 2/2006 | Marshall |
| 7,004,945 B2 | 3/2006 | Boyd et al. |
| 7,008,433 B2 | 3/2006 | Voellmicke et al. |
| 7,018,460 B2 | 3/2006 | Xu et al. |
| 7,022,133 B2 | 4/2006 | Yee et al. |
| 7,029,468 B2 | 4/2006 | Honebrink |
| 7,044,954 B2 | 5/2006 | Reiley et al. |
| 7,059,330 B1 | 6/2006 | Makower et al. |
| 7,063,682 B1 | 6/2006 | Whayne et al. |
| 7,066,942 B2 | 6/2006 | Treace |
| RE39,196 E | 7/2006 | Ying et al. |
| 7,081,122 B1 | 7/2006 | Reiley et al. |
| 7,081,161 B2 | 7/2006 | Genge et al. |
| 7,091,258 B2 | 8/2006 | Neubert et al. |
| 7,091,260 B2 | 8/2006 | Kühn |
| 7,094,202 B2 | 8/2006 | Nobis et al. |
| 7,094,286 B2 | 8/2006 | Liu |
| 7,108,696 B2 | 9/2006 | Daniel et al. |
| 7,109,254 B2 | 9/2006 | Müller et al. |
| 7,112,205 B2 | 9/2006 | Carrison |
| 7,114,501 B2 | 10/2006 | Johnson et al. |
| 7,138,442 B2 | 11/2006 | Smith et al. |
| 7,153,306 B2 | 12/2006 | Ralph et al. |
| 7,153,307 B2 | 12/2006 | Scribner et al. |
| 7,156,843 B2 | 1/2007 | Skarda |
| 7,156,845 B2 | 1/2007 | Mulier |
| 7,160,296 B2 | 1/2007 | Pearson et al. |
| 7,166,121 B2 | 1/2007 | Reiley et al. |
| 7,172,629 B2 | 2/2007 | McKay et al. |
| 7,179,255 B2 | 2/2007 | Lettice et al. |
| 7,186,234 B2 | 3/2007 | Dahla et al. |
| 7,186,761 B2 | 3/2007 | Soffiati et al. |
| 7,226,481 B2 | 6/2007 | Kuslich et al. |
| 7,252,671 B2 | 8/2007 | Scribner et al. |
| 7,267,683 B2 | 9/2007 | Sharkey et al. |
| 7,270,661 B2 | 9/2007 | Dahla et al. |
| 7,294,127 B2 | 11/2007 | Leung |
| 7,465,318 B2 | 12/2008 | Sennett et al. |
| 7,480,533 B2 | 1/2009 | Cosman et al. |
| 7,503,920 B2 | 3/2009 | Siegal |
| 7,544,196 B2 | 6/2009 | Bagga et al. |
| 7,559,932 B2 | 7/2009 | Truckai et al. |
| 7,569,054 B2 | 8/2009 | Michelson |
| 7,572,263 B2 | 8/2009 | Preissman |
| 7,591,822 B2 | 9/2009 | Olson, Jr. et al. |
| 7,625,364 B2 | 12/2009 | Corcoran et al. |
| 7,641,664 B2 | 1/2010 | Pagano |
| 7,731,720 B2 | 6/2010 | Sand et al. |
| 7,811,291 B2 | 10/2010 | Liu et al. |
| 7,824,403 B2 | 11/2010 | Vaska |
| 7,842,041 B2 | 11/2010 | Liu et al. |
| 7,887,543 B2 | 2/2011 | Sand et al. |
| 7,905,884 B2 | 3/2011 | Simonton et al. |
| 7,918,874 B2 | 4/2011 | Siegal |
| 7,972,340 B2 | 7/2011 | Sand et al. |
| 7,976,542 B1 | 7/2011 | Cosman |
| 8,034,071 B2 | 10/2011 | Scribner et al. |
| 8,246,627 B2 | 8/2012 | Vanleeuwen et al. |
| 8,518,036 B2 | 8/2013 | Leung |
| 8,583,260 B2 | 11/2013 | Knudson |
| 8,591,507 B2 | 11/2013 | Kramer et al. |
| 8,663,226 B2 | 3/2014 | Germain |
| RE44,883 E | 5/2014 | Cha |
| 8,758,349 B2 | 6/2014 | Germain et al. |
| 8,827,981 B2 | 9/2014 | Liu et al. |
| 8,864,760 B2 | 10/2014 | Kramer et al. |
| 8,936,631 B2 | 1/2015 | Nguyen et al. |
| 9,113,974 B2 | 8/2015 | Germain |
| 9,125,671 B2 | 9/2015 | Germain et al. |
| 9,161,809 B2 | 10/2015 | Germain et al. |
| 9,421,057 B2 | 8/2016 | Germain |
| 9,743,938 B2 | 8/2017 | Germain et al. |
| 2001/0011174 A1 | 8/2001 | Reiley et al. |
| 2001/0023349 A1 | 9/2001 | Van et al. |
| 2002/0007180 A1 | 1/2002 | Wittenberger et al. |
| 2002/0013600 A1 | 1/2002 | Scribner et al. |
| 2002/0016583 A1 | 2/2002 | Cragg |
| 2002/0026195 A1 | 2/2002 | Layne et al. |
| 2002/0026197 A1 | 2/2002 | Foley et al. |
| 2002/0068929 A1 | 6/2002 | Zvuloni |
| 2002/0068974 A1 | 6/2002 | Kuslich et al. |
| 2002/0077595 A1 | 6/2002 | Hundertmark et al. |
| 2002/0082605 A1 | 6/2002 | Reiley et al. |
| 2002/0115742 A1 | 8/2002 | Trieu et al. |
| 2002/0128638 A1 | 9/2002 | Chauvel et al. |
| 2002/0133148 A1 | 9/2002 | Daniel et al. |
| 2002/0156483 A1 | 10/2002 | Voellmicke et al. |
| 2002/0188299 A1 | 12/2002 | Reiley et al. |
| 2002/0188300 A1 | 12/2002 | Arramon et al. |
| 2003/0014094 A1 | 1/2003 | Iammack et al. |
| 2003/0032929 A1 | 2/2003 | McGuckin |
| 2003/0036763 A1 | 2/2003 | Bhatnagar et al. |
| 2003/0043963 A1 | 3/2003 | Yamagami et al. |
| 2003/0050644 A1 | 3/2003 | Boucher et al. |
| 2003/0069522 A1 | 4/2003 | Jasobsen et al. |
| 2003/0073979 A1 | 4/2003 | Naimark et al. |
| 2003/0130664 A1 | 7/2003 | Boucher et al. |
| 2003/0163085 A1 | 8/2003 | Tanner et al. |
| 2003/0171744 A1 | 9/2003 | Leung et al. |
| 2003/0191489 A1 | 10/2003 | Reiley et al. |
| 2003/0195547 A1 | 10/2003 | Scribner et al. |
| 2003/0212394 A1 | 11/2003 | Pearson et al. |
| 2003/0212395 A1 | 11/2003 | Woloszko et al. |
| 2003/0220414 A1 | 11/2003 | Axen et al. |
| 2003/0225432 A1 | 12/2003 | Baptiste et al. |
| 2003/0233096 A1 | 12/2003 | Osorio et al. |
| 2004/0023384 A1 | 2/2004 | Fukaya |
| 2004/0023784 A1 | 2/2004 | Yu et al. |
| 2004/0024081 A1 | 2/2004 | Trieu et al. |
| 2004/0024398 A1 | 2/2004 | Hovda et al. |
| 2004/0024409 A1 | 2/2004 | Sand et al. |
| 2004/0024410 A1 | 2/2004 | Olson et al. |
| 2004/0034384 A1 | 2/2004 | Fukaya |
| 2004/0044096 A1 | 3/2004 | Smith et al. |
| 2004/0044350 A1 | 3/2004 | Martin et al. |
| 2004/0059328 A1 | 3/2004 | Daniel et al. |
| 2004/0087936 A1 | 5/2004 | Stern et al. |
| 2004/0087994 A1 | 5/2004 | Suddaby |
| 2004/0092946 A1 | 5/2004 | Bagga et al. |
| 2004/0097612 A1 | 5/2004 | Rosenberg et al. |
| 2004/0111136 A1 | 6/2004 | Sharkey et al. |
| 2004/0127987 A1 | 7/2004 | Evans et al. |
| 2004/0133208 A1 | 7/2004 | Weikel et al. |
| 2004/0138758 A1 | 7/2004 | Evans et al. |
| 2004/0153064 A1 | 8/2004 | Foley et al. |
| 2004/0153115 A1 | 8/2004 | Reiley et al. |

(56) References Cited

U.S. PATENT DOCUMENTS

| | | |
|---|---|---|
| 2004/0158237 A1 | 8/2004 | Abboud et al. |
| 2004/0167561 A1 | 8/2004 | Boucher et al. |
| 2004/0167562 A1 | 8/2004 | Osorio et al. |
| 2004/0167625 A1 | 8/2004 | Beyar et al. |
| 2004/0210231 A1 | 10/2004 | Broucher et al. |
| 2004/0215343 A1 | 10/2004 | Hochschuler et al. |
| 2004/0220577 A1 | 11/2004 | Cragg |
| 2004/0220680 A1 | 11/2004 | Yamamoto et al. |
| 2004/0225296 A1 | 11/2004 | Reiss et al. |
| 2004/0226479 A1 | 11/2004 | Lyles et al. |
| 2004/0230309 A1 | 11/2004 | Dimauro et al. |
| 2004/0236186 A1 | 11/2004 | Chu |
| 2004/0247644 A1 | 12/2004 | Bratt et al. |
| 2004/0267271 A9 | 12/2004 | Scribner et al. |
| 2005/0027245 A1 | 2/2005 | Sachdeva et al. |
| 2005/0033303 A1 | 2/2005 | Chappuis et al. |
| 2005/0038383 A1 | 2/2005 | Kelley et al. |
| 2005/0038422 A1 | 2/2005 | Maurice |
| 2005/0043737 A1 | 2/2005 | Reiley et al. |
| 2005/0055030 A1 | 3/2005 | Falahee |
| 2005/0060030 A1 | 3/2005 | Ashinski et al. |
| 2005/0070844 A1 | 3/2005 | Chow et al. |
| 2005/0070912 A1 | 3/2005 | Voellmicke |
| 2005/0070915 A1 | 3/2005 | Mazzuca et al. |
| 2005/0090852 A1 | 4/2005 | Layne et al. |
| 2005/0113836 A1 | 5/2005 | Lozier et al. |
| 2005/0119650 A1 | 6/2005 | Sanders et al. |
| 2005/0124989 A1 | 6/2005 | Suddaby |
| 2005/0143827 A1 | 6/2005 | Globerman et al. |
| 2005/0171593 A1 | 8/2005 | Whirley et al. |
| 2005/0177168 A1 | 8/2005 | Brunnett et al. |
| 2005/0177210 A1 | 8/2005 | Leung et al. |
| 2005/0182412 A1 | 8/2005 | Johnson et al. |
| 2005/0182413 A1 | 8/2005 | Johnson et al. |
| 2005/0187556 A1 | 8/2005 | Stack et al. |
| 2005/0199156 A1 | 9/2005 | Khairoun et al. |
| 2005/0209557 A1 | 9/2005 | Carroll et al. |
| 2005/0216018 A1 | 9/2005 | Sennett |
| 2005/0228391 A1 | 10/2005 | Levy et al. |
| 2005/0234425 A1 | 10/2005 | Miller et al. |
| 2005/0240193 A1 | 10/2005 | Layne et al. |
| 2005/0251266 A1 | 11/2005 | Maspero et al. |
| 2005/0251267 A1 | 11/2005 | Winterbottom et al. |
| 2005/0261683 A1 | 11/2005 | Veldhuizen et al. |
| 2005/0283148 A1 | 12/2005 | Janssen |
| 2005/0287771 A1 | 12/2005 | Seamons et al. |
| 2006/0024348 A1 | 2/2006 | Engqvist et al. |
| 2006/0025763 A1 | 2/2006 | Nelson et al. |
| 2006/0041033 A1 | 2/2006 | Bisig et al. |
| 2006/0052743 A1 | 3/2006 | Reynolds |
| 2006/0064101 A1 | 3/2006 | Arramon |
| 2006/0074433 A1 | 4/2006 | McGill et al. |
| 2006/0084977 A1 | 4/2006 | Lieberman |
| 2006/0085009 A1 | 4/2006 | Truckai et al. |
| 2006/0100635 A1 | 5/2006 | Reiley et al. |
| 2006/0100706 A1 | 5/2006 | Shadduck et al. |
| 2006/0106392 A1 | 5/2006 | Embry |
| 2006/0106459 A1 | 5/2006 | Truckai et al. |
| 2006/0116689 A1 | 6/2006 | Albans et al. |
| 2006/0116690 A1 | 6/2006 | Pagano |
| 2006/0122623 A1 | 6/2006 | Truckai et al. |
| 2006/0142732 A1 | 6/2006 | Karmarkar et al. |
| 2006/0149268 A1 | 7/2006 | Truckai et al. |
| 2006/0149281 A1 | 7/2006 | Reiley et al. |
| 2006/0156959 A1 | 7/2006 | Engqvist et al. |
| 2006/0184106 A1 | 8/2006 | McDaniel et al. |
| 2006/0184192 A1 | 8/2006 | Markworth et al. |
| 2006/0200121 A1 | 9/2006 | Mowery |
| 2006/0206116 A1 | 9/2006 | Yeung |
| 2006/0206136 A1 | 9/2006 | Sachdeva et al. |
| 2006/0217704 A1 | 9/2006 | Cockburn et al. |
| 2006/0217736 A1 | 9/2006 | Kaneko |
| 2006/0229625 A1 | 10/2006 | Truckai et al. |
| 2006/0229631 A1 | 10/2006 | Reiley et al. |
| 2006/0235417 A1 | 10/2006 | Sala |
| 2006/0259023 A1 | 11/2006 | Abboud et al. |
| 2006/0264819 A1 | 11/2006 | Fischer et al. |
| 2006/0264945 A1 | 11/2006 | Edidin et al. |
| 2006/0266372 A1 | 11/2006 | Miller et al. |
| 2006/0270750 A1 | 11/2006 | Almen et al. |
| 2006/0271061 A1 | 11/2006 | Beyar et al. |
| 2006/0276797 A1 | 12/2006 | Botimer |
| 2006/0276819 A1 | 12/2006 | Osorio et al. |
| 2006/0293687 A1 | 12/2006 | Bogert |
| 2007/0006692 A1 | 1/2007 | Phan |
| 2007/0010845 A1 | 1/2007 | Gong et al. |
| 2007/0016130 A1 | 1/2007 | Leeflang et al. |
| 2007/0016211 A1 | 1/2007 | Botimer |
| 2007/0021769 A1 | 1/2007 | Scribner et al. |
| 2007/0043373 A1 | 2/2007 | Sala |
| 2007/0055201 A1 | 3/2007 | Seto et al. |
| 2007/0055260 A1 | 3/2007 | Cragg |
| 2007/0055266 A1 | 3/2007 | Osorio et al. |
| 2007/0055275 A1 | 3/2007 | Schaller |
| 2007/0055277 A1 | 3/2007 | Osorio et al. |
| 2007/0055278 A1 | 3/2007 | Osorio et al. |
| 2007/0055279 A1 | 3/2007 | Sand et al. |
| 2007/0055281 A1 | 3/2007 | Osorio et al. |
| 2007/0055283 A1 | 3/2007 | Scribner |
| 2007/0055284 A1 | 3/2007 | Osorio |
| 2007/0055285 A1 | 3/2007 | Osorio et al. |
| 2007/0055300 A1 | 3/2007 | Osorio et al. |
| 2007/0055382 A1 | 3/2007 | Osorio et al. |
| 2007/0059281 A1 | 3/2007 | Moseley et al. |
| 2007/0067034 A1 | 3/2007 | Chirico et al. |
| 2007/0093840 A1 | 4/2007 | Pacelli |
| 2007/0114248 A1 | 5/2007 | Kovac |
| 2007/0118142 A1 | 5/2007 | Krueger et al. |
| 2007/0118143 A1 | 5/2007 | Ralph et al. |
| 2007/0142842 A1 | 6/2007 | Krueger et al. |
| 2007/0156130 A1 | 7/2007 | Thistle |
| 2007/0162042 A1 | 7/2007 | Dunker |
| 2007/0173939 A1 | 7/2007 | Kim et al. |
| 2007/0185231 A1 | 8/2007 | Liu et al. |
| 2007/0197935 A1 | 8/2007 | Reiley |
| 2007/0198023 A1 | 8/2007 | Sand et al. |
| 2007/0203500 A1 | 8/2007 | Gordon |
| 2007/0211563 A1 | 9/2007 | DeVries |
| 2007/0233146 A1 | 10/2007 | Henniges et al. |
| 2007/0260223 A1 | 11/2007 | Scheibe et al. |
| 2007/0260257 A1 | 11/2007 | Phan |
| 2007/0270876 A1 | 11/2007 | Kuo et al. |
| 2007/0276319 A1 | 11/2007 | Betts |
| 2007/0282305 A1 | 12/2007 | Goldfarb et al. |
| 2008/0004615 A1 | 1/2008 | Woloszko et al. |
| 2008/0015664 A1* | 1/2008 | Podhajsky ............ A61B 34/10 607/99 |
| 2008/0033422 A1 | 2/2008 | Turner et al. |
| 2008/0058725 A1 | 3/2008 | Scribner et al. |
| 2008/0058821 A1 | 3/2008 | Maurer et al. |
| 2008/0058827 A1 | 3/2008 | Osorio et al. |
| 2008/0058840 A1 | 3/2008 | Albrecht |
| 2008/0065020 A1 | 3/2008 | Ralph et al. |
| 2008/0065087 A1 | 3/2008 | Osorio et al. |
| 2008/0065190 A1 | 3/2008 | Osorio et al. |
| 2008/0086142 A1 | 4/2008 | Kohm et al. |
| 2008/0125775 A1* | 5/2008 | Morris ............... A61B 18/1477 606/50 |
| 2008/0140079 A1 | 6/2008 | Osorio et al. |
| 2008/0183165 A1 | 7/2008 | Buysee et al. |
| 2008/0183265 A1 | 7/2008 | Bly |
| 2008/0195112 A1 | 8/2008 | Liu et al. |
| 2008/0208255 A1 | 8/2008 | Siegal |
| 2008/0221608 A1 | 9/2008 | Betts |
| 2008/0228192 A1 | 9/2008 | Beyer et al. |
| 2008/0249481 A1 | 10/2008 | Crainich |
| 2008/0249525 A1 | 10/2008 | Lee et al. |
| 2008/0255571 A1 | 10/2008 | Truckai et al. |
| 2008/0269766 A1 | 10/2008 | Justis |
| 2008/0269796 A1 | 10/2008 | Reiley et al. |
| 2008/0287741 A1 | 11/2008 | Ostrovsky et al. |
| 2008/0294167 A1 | 11/2008 | Schumacher et al. |
| 2009/0076517 A1 | 3/2009 | Reiley et al. |
| 2009/0105775 A1 | 4/2009 | Mitchell et al. |

(56) References Cited

U.S. PATENT DOCUMENTS

| | | |
|---|---|---|
| 2009/0131867 A1 | 5/2009 | Liu et al. |
| 2009/0131886 A1 | 5/2009 | Liu et al. |
| 2009/0131945 A1 | 5/2009 | Iu et al. |
| 2009/0131948 A1 | 5/2009 | Liu |
| 2009/0131950 A1 | 5/2009 | Liu et al. |
| 2009/0131986 A1 | 5/2009 | Lee |
| 2009/0182427 A1 | 7/2009 | Liu et al. |
| 2009/0198243 A1 | 8/2009 | Melsheimer |
| 2009/0264862 A1 | 10/2009 | Neidert et al. |
| 2009/0264892 A1 | 10/2009 | Beyar et al. |
| 2009/0292289 A9 | 11/2009 | Sand et al. |
| 2009/0293687 A1 | 12/2009 | Nino et al. |
| 2009/0299282 A1 | 12/2009 | Lau et al. |
| 2010/0057087 A1 | 3/2010 | Cha |
| 2010/0076476 A1 | 3/2010 | To et al. |
| 2010/0082033 A1 | 4/2010 | Germain |
| 2010/0114184 A1 | 5/2010 | Degtyar |
| 2010/0121332 A1 | 5/2010 | Crainich et al. |
| 2010/0152724 A1 | 6/2010 | Marion et al. |
| 2010/0160922 A1 | 6/2010 | Liu et al. |
| 2010/0211076 A1 | 8/2010 | Germain et al. |
| 2010/0274270 A1 | 10/2010 | Patel |
| 2010/0298832 A1 | 11/2010 | Au et al. |
| 2011/0034884 A9 | 2/2011 | Pellegrino et al. |
| 2011/0098701 A1 | 4/2011 | McIntyre et al. |
| 2011/0160737 A1 | 6/2011 | Steffen et al. |
| 2011/0251615 A1 | 10/2011 | Truckai et al. |
| 2011/0295261 A1 | 12/2011 | Germain |
| 2011/0295262 A1 | 12/2011 | Germain et al. |
| 2011/0301590 A1 | 12/2011 | Podhajsky et al. |
| 2012/0065543 A1 | 3/2012 | Ireland |
| 2012/0130381 A1 | 5/2012 | Germain |
| 2012/0143298 A1 | 6/2012 | Just et al. |
| 2012/0158004 A1 | 6/2012 | Burger et al. |
| 2012/0191095 A1 | 7/2012 | Burger et al. |
| 2012/0239049 A1 | 9/2012 | Truckai |
| 2012/0265186 A1 | 10/2012 | Burger et al. |
| 2012/0277582 A1 | 11/2012 | Mafi |
| 2012/0277730 A1 | 11/2012 | Salahieh |
| 2012/0330180 A1 | 12/2012 | Pellegrino et al. |
| 2012/0330301 A1 | 12/2012 | Pellegrino et al. |
| 2013/0006232 A1 | 1/2013 | Pellegrino |
| 2013/0006257 A1 | 1/2013 | Lee |
| 2013/0041377 A1 | 2/2013 | Kuntz |
| 2013/0072941 A1 | 3/2013 | Tan-Malecki et al. |
| 2013/0231654 A1 | 9/2013 | Germain |
| 2013/0237795 A1 | 9/2013 | Carr |
| 2013/0261615 A1 | 10/2013 | Kramer et al. |
| 2013/0261621 A1 | 10/2013 | Kramer et al. |
| 2013/0345709 A1 | 12/2013 | Burger et al. |
| 2014/0135779 A1 | 5/2014 | Germain |
| 2014/0163566 A1 | 6/2014 | Phan et al. |
| 2014/0236144 A1 | 8/2014 | Krueger et al. |
| 2014/0257046 A1* | 9/2014 | Steven .................. A61B 90/98 600/301 |
| 2014/0316413 A1 | 10/2014 | Burger et al. |
| 2014/0350542 A1 | 11/2014 | Kramer et al. |
| 2014/0371740 A1 | 12/2014 | Germain et al. |
| 2015/0216594 A1 | 8/2015 | Prakash |
| 2015/0265333 A1 | 9/2015 | Shin et al. |
| 2015/0297246 A1 | 10/2015 | Patel et al. |
| 2015/0313614 A1 | 11/2015 | Germain |
| 2016/0066984 A1* | 3/2016 | Janssen ............ A61B 18/1477 606/34 |
| 2016/0228131 A1 | 8/2016 | Brockman et al. |
| 2016/0310193 A1 | 10/2016 | Lv et al. |
| 2017/0095291 A1 | 4/2017 | Harrington |
| 2017/0105798 A1 | 4/2017 | Allison |
| 2018/0078170 A1* | 3/2018 | Panescu ................ A61B 34/20 |
| 2018/0147006 A1 | 5/2018 | Purdy |
| 2018/0147007 A1 | 5/2018 | Purdy |
| 2019/0357971 A1* | 11/2019 | Adi .................... A61B 18/1477 |
| 2020/0022709 A1 | 1/2020 | Burger et al. |
| 2020/0025387 A1* | 1/2020 | Suel, II ................. F24C 7/083 |
| 2020/0078066 A1 | 3/2020 | Purdy et al. |
| 2020/0146744 A1 | 5/2020 | Defosset et al. |
| 2020/0375725 A1 | 12/2020 | Chobotov et al. |
| 2020/0390449 A1 | 12/2020 | Purdy et al. |
| 2021/0236200 A1* | 8/2021 | McGregor ......... A61B 18/1206 |

FOREIGN PATENT DOCUMENTS

| | | |
|---|---|---|
| CN | 2841051 | 11/2006 |
| CN | 102500036 A | 6/2012 |
| DE | 20314010 | 1/2015 |
| EP | 1459691 | 9/2004 |
| JP | 2004242936 | 9/2004 |
| JP | 2008510530 | 4/2008 |
| JP | 2008528081 | 7/2008 |
| JP | 2008541878 | 11/2008 |
| JP | 2010063887 | 3/2010 |
| JP | 2011500156 | 1/2011 |
| KR | 101342906 | 12/2013 |
| WO | 1993004634 | 3/1993 |
| WO | 1996013297 | 5/1996 |
| WO | 1996020752 | 7/1996 |
| WO | 1997003611 | 2/1997 |
| WO | 2002003870 | 1/2002 |
| WO | 2003101308 | 12/2003 |
| WO | 2005039390 | 5/2005 |
| WO | 2005122938 | 12/2005 |
| WO | 2007036815 | 4/2007 |
| WO | 2007087400 | 8/2007 |
| WO | 2008076330 | 6/2008 |
| WO | 2008084479 | 7/2008 |
| WO | 2009155319 | 12/2009 |
| WO | 2010039894 | 4/2010 |
| WO | 2010081187 | 7/2010 |
| WO | 2010135602 | 11/2010 |
| WO | 2010135606 | 11/2010 |
| WO | 2011066465 | 6/2011 |
| WO | 2011114602 | 9/2011 |
| WO | 2011137357 | 11/2011 |
| WO | 2011137377 | 11/2011 |
| WO | 2012071464 | 5/2012 |
| WO | 2013147990 | 10/2013 |
| WO | 2014093673 | 6/2014 |
| WO | 2016183178 | 11/2016 |

OTHER PUBLICATIONS

Office Action dated Nov. 27, 2020 for U.S. Appl. No. 15/822,944.
Notice of Allowance dated Dec. 28, 2017 for U.S. Appl. No. 15/211,359.
Notice of Allowance dated Aug. 31, 2016 for U.S. Appl. No. 14/887,007.
Office Action dated Jan. 18, 2017 for U.S. Appl. No. 14/815,620.
Office Action dated Jan. 26, 2011 for U.S. Appl. No. 11/941,764.
Office Action dated Jan. 26, 2017 for U.S. Appl. No. 14/815,812.
Office Action dated Feb. 3, 2016 for U.S. Appl. No. 13/853,397.
Office Action dated Feb. 10, 2015 for U.S. Appl. No. 13/083,411.
Office Action dated Feb. 23, 2010 for U.S. Appl. No. 11/941,733.
Office Action dated Feb. 23, 2010 for U.S. Appl. No. 11/941,764.
Office Action dated Mar. 1, 2017 for U.S. Appl. No. 15/211,359.
Office Action dated Mar. 21, 2011 for U.S. Appl. No. 11/941,764.
Office Action dated Mar. 21, 2011 for U.S. Appl. No. 12/029,428.
Office Action dated Apr. 19, 2018 for U.S. Appl. No. 15/388,598.
Office Action dated Apr. 24, 2017 for U.S. Appl. No. 14/453,427.
Office Action dated Apr. 26, 2010 for U.S. Appl. No. 12/029,428.
Office Action dated May 1, 2009 for U.S. Appl. No. 12/261,987.
Office Action dated May 5, 2010 for U.S. Appl. No. 11/941,764.
Office Action dated May 6, 2019 for U.S. Appl. No. 15/675,315.
Office Action dated May 13, 2009 for U.S. Appl. No. 12/029,428.
Office Action dated May 17, 2010 for U.S. Appl. No. 12/261,987.
Office Action dated May 21, 2014 for U.S. Appl. No. 13/098,116.
Office Action dated May 24, 2012 for U.S. Appl. No. 12/578,455.
Office Action dated May 31, 2016 for U.S. Appl. No. 14/815,620.
Office Action dated Jun. 4, 2018 for U.S. Appl. No. 15/349,715.
Office Action dated Jun. 8, 2009 for U.S. Appl. No. 11/941,764.
Office Action dated Jun. 12, 2009 for U.S. Appl. No. 11/941,733.

(56) References Cited

OTHER PUBLICATIONS

Office Action dated Jun. 21, 2013 for U.S. Appl. No. 13/215,098.
Office Action dated Jun. 22, 2018 for U.S. Appl. No. 15/917,454.
Office Action dated Jun. 25, 2015 for U.S. Appl. No. 13/853,397.
Office Action dated Jun. 29, 2018 for U.S. Appl. No. 15/449,591.
Office Action dated Dec. 11, 2009 for U.S. Appl. No. 12/261,987.
Office Action dated Dec. 20, 2019 for U.S. Appl. No. 15/862,441.
Office Action dated Dec. 26, 2019 for U.S. Appl. No. 15/822,864.
Office Action dated Feb. 27, 2013 for U.S. Appl. No. 12/578,455.
Office Action dated Jul. 12, 2016 for U.S. Appl. No. 14/887,007.
Office Action dated Sep. 10, 2013 for U.S. Appl. No. 12/571,174.
Disc-O-Tech confidence Cement System at http://www.disc-o-tech.com/Articles/Article.asp?CategoryID=4&ArticleID=168 accessed, Dec. 3, 2007.
Dai, et al.,Bone-Particle-Impregnated Bone Cement: an in vivo weight-bearing study, Journal Biomedical Materials Search, vol. 25 ,Jul. 30, 1990 ,141-156.
Hasenwinkel, et al.,"A Novel High-Viscosity, Two-Solution Acrylic Bone Cement: Effect of Chemical Composition on Properties", J. Biomed Mater. Res. vol. 47, No. 1 ,1999 ,36-45.
Klawitter, et al.,Application of Porous Ceramics for the Attachment of Load Bearing Internal Orthopedic Applications, J. Biomed. Mater. Res. Symp., 2(1) ,1972 ,61-229.
Liu, et al.,Bone-Particle-Impregnanted Bone Cement: An In Vitro Study, Journal of Biomedical Materials Research, vol. 21 ,1987 ,247-261.
Park, et al.,Biomaterials: An Introduction—Second Edition, Plenum Press , 1992 ,177-178.
Park, et al.,The Materials Properties of Bone-Particle Impregnated PMMA, Journal of Biomedical Engineering, vol. 108 ,1986 ,141-148.
Notice of Allowance dated Mar. 31, 2021 for U.S. Appl. No. 15/822,864.
European Search Report dated May 29, 2020 for EP17874650.9.
European Search Report dated Jun. 16, 2020 for EP17863626.2.
European Search Report dated Jul. 1, 2020 for EP17878602.6.
Office Action dated Jun. 10, 2020 for U.S. Appl. No. 15/822,944.
Office Action dated Jun. 11, 2020 for U.S. Appl. No. 15/822,864.
Office Action dated Jul. 11, 2017 for U.S. Appl. No. 14/815,812.
Office Action dated Jul. 12, 2010 for U.S. Appl. No. 11/941,764.
Office Action dated Jul. 12, 2017 for U.S. Appl. No. 13/083,411.
Office Action dated Jul. 25, 2011 for U.S. Appl. No. 11/941,733.
Office Action dated Jul. 29, 2013 for U.S. Appl. No. 13/098,116.
Office Action dated Jul. 30, 2013 for U.S. Appl. No. 13/083,411.
Office Action dated Sep. 1, 2010 for U.S. Appl. No. 12/029,428.
Office Action dated Sep. 6, 2017 for U.S. Appl. No. 15/211,359.
Office Action dated Sep. 26, 2017 for U.S. Appl. No. 15/388,598.
Office Action dated Oct. 2, 2018 for U.S. Appl. No. 14/139,372.
Office Action dated Oct. 30, 2018 for U.S. Appl. No. 15/349,715.
Office Action dated Nov. 3, 2008 for U.S. Appl. No. 11/941,764.
Office Action dated Nov. 3, 2008 for U.S. Appl. No. 12/029,428.
Office Action dated Nov. 5, 2008 for U.S. Appl. No. 11/941,733.
Office Action dated Nov. 7, 2019 for U.S. Appl. No. 15/675,315.
Office Action dated Nov. 12, 2013 for U.S. Appl. No. 13/083,411.
Office Action dated Nov. 25, 2016 for U.S. Appl. No. 13/083,411.
Office Action dated Dec. 2, 2009 for U.S. Appl. No. 12/029,428.
Office Action dated Dec. 3, 2012 for U.S. Appl. No. 12/571,174.
Office Action dated Dec. 9, 2009 for U.S. Appl. No. 12/262,064.
International Search Report and Written Opinion dated Apr. 8, 2020 for PCT/US2019060279.
Notice of Allowance dated Feb. 19, 2020 for U.S. Appl. No. 15/675,315.
International Search Report and Written Opinion dated Apr. 8, 2020 for PCT/US2019/060273.
European Examination Report dated Dec. 19, 2017 for EP13767383.6.
European Search Report dated Jan. 7, 2019 for EP16793433.0.
European Search Report dated Jun. 8, 2017 for EP17154660.9.
European Search Report dated Nov. 15, 2017 for EP09818476.5.
European Search Report dated Nov. 16, 2016 for EP14772615.2.
International Search Report and Written Opinion dated Jan. 9, 2012 for PCT/US2011/034185.
International Search Report and Written Opinion dated Jan. 22, 2009 for PCT/US2008/83698.
International Search Report and Written Opinion dated Feb. 7, 2018 for PCT/US2017/058303.
International Search Report and Written Opinion dated Feb. 21, 2018 for PCT/US2017/063281.
International Search Report and Written Opinion dated Mar. 30, 2018 for PCT/US2017/065328.
International Search Report and Written Opinion dated Apr. 23, 2016 for PCT/US2018/012372.
International Search Report and Written Opinion dated Jul. 20, 2010 for PCT/US2010/035687.
International Search Report and Written Opinion dated Jul. 26, 2011 for PCT/US2011/034628.
International Search Report and Written Opinion dated Aug. 25, 2009 for PCT/US2009/035726.
International Search Report and Written Opinion dated Nov. 20, 2009 for PCT/US2009/059113.
Notice of Allowance dated Jan. 4, 2017 for U.S. Appl. No. 13/302,927.
Notice of Allowance dated Jan. 18, 2017 for U.S. Appl. No. 13/097,998.
Notice of Allowance dated Feb. 21, 2019 for U.S. Appl. No. 14/139,372.
Notice of Allowance dated Apr. 3, 2019 for U.S. Appl. No. 15/349,715.
Notice of Allowance dated Apr. 9, 2014 for U.S. Appl. No. 12/578,455.
Notice of Allowance dated Apr. 23, 2018 for U.S. Appl. No. 13/083,411.
Notice of Allowance dated May 3, 2017 for U.S. Appl. No. 14/815,620.
Notice of Allowance dated May 11, 2018 for U.S. Appl. No. 14/453,427.
Notice of Allowance dated May 26, 2015 for U.S. Appl. No. 13/098,116.
Notice of Allowance dated Aug. 8, 2019 for U.S. Appl. No. 15/836,125.
Notice of Allowance dated Aug. 9, 2019 for U.S. Appl. No. 15/836,241.
Notice of Allowance dated Aug. 24, 2018 for U.S. Appl. No. 15/388,598.
Notice of Allowance dated Sep. 20, 2019 for U.S. Appl. No. 15/793,509.
Notice of Allowance dated Oct. 28, 2016 for U.S. Appl. No. 13/853,397.
Notice of Allowance dated Nov. 8, 2013 for U.S. Appl. No. 12/578,455.
Notice of Allowance dated Nov. 9, 2017 for U.S. Appl. No. 14/815,812.
Notice of Allowance dated Nov. 18, 2016 for U.S. Appl. No. 13/097,998.
Notice of Allowance dated Nov. 25, 2013 for U.S. Appl. No. 12/571,174.
Notice of Allowance dated Nov. 25, 2016 for U.S. Appl. No. 13/853,397.
Notice of Allowance dated Dec. 13, 2018 for U.S. Appl. No. 15/917,454.
Notice of Allowance dated May 27, 2021 for U.S. Appl. No. 15/822,944.
Office Action dated May 7, 2021 for U.S. Appl. No. 16/417,502.
European Search Report dated Mar. 14, 2023 for EP178746509.
Office Action dated Aug. 10, 2015 for U.S. Appl. No. 14/044,050.
Office Action dated Aug. 19, 2022 for U.S. Appl. No. 16/881,927.
Office Action dated Aug. 22, 2019 for U.S. Appl. No. 14/207,344.
Office Action dated Aug. 29, 2014 for U.S. Appl. No. 14/152,590.
Office Action dated Sep. 9, 2016 for U.S. Appl. No. 14/081,504.
Office Action dated Sep. 9, 2016 for U.S. Appl. No. 14/207,344.
Office Action dated Sep. 11, 2017 for U.S. Appl. No. 14/832,422.
Office Action dated Sep. 23, 2016 for U.S. Appl. No. 14/152,590.
Office Action dated Sep. 24, 2014 for U.S. Appl. No. 14/031,746.
Office Action dated Sep. 27, 2016 for U.S. Appl. No. 13/827,790.
Office Action dated Sep. 28, 2017 for U.S. Appl. No. 14/207,344.
Office Action dated Oct. 6, 2016 for U.S. Appl. No. 13/360,444.

(56) References Cited

OTHER PUBLICATIONS

Office Action dated Oct. 6, 2016 for U.S. Appl. No. 13/742,025.
Office Action dated Oct. 7, 2019 for U.S. Appl. No. 13/360,444.
Office Action dated Oct. 7, 2019 for U.S. Appl. No. 14/152,590.
Office Action dated Oct. 10, 2014 for U.S. Appl. No. 13/742,025.
Office Action dated Oct. 15, 2015 for U.S. Appl. No. 13/827,790.
Office Action dated Oct. 20, 2017 for U.S. Appl. No. 13/826,618.
Office Action dated Oct. 26, 2016 for U.S. Appl. No. 13/742,077.
Office Action dated Nov. 2, 2015 for U.S. Appl. No. 13/742,077.
Office Action dated Nov. 17, 2016 for U.S. Appl. No. 13/829,493.
Office Action dated Nov. 17, 2017 for U.S. Appl. No. 13/360,444.
Office Action dated Nov. 18, 2016 for U.S. Appl. No. 13/826,618.
Office Action dated Nov. 20, 2015 for U.S. Appl. No. 13/826,618.
Office Action dated Nov. 21, 2017 for U.S. Appl. No. 14/152,590.
Office Action dated Dec. 18, 2015 for U.S. Appl. No. 14/081,504.
Office Action dated Dec. 23, 2020 for U.S. Appl. No. 13/827,790.
Office Action dated Dec. 24, 2021 for U.S. Appl. No. 16/877,259.
Office Action dated Dec. 28, 2017 for U.S. Appl. No. 13/827,790.
Office Action dated Dec. 29, 2017 for U.S. Appl. No. 14/081,504.
"Shuttle® and CT-Core® Semi-Automatic Devices Updated to the website between Nov. 8, 2012-Jan. 24, 2013", Accessed website on Jun. 27, 2014 at http://www.healthcare.com/qb/int_radiology.html.
Arras, et al., "Electrospinning of Aligned Fibers with Adjustable Orientation Using Auxiliary Electrodes", Sci. Technol. Adv. Mater., 13, Jan. 1, 2012.
Office Action dated Jan. 12, 2022 for U.S. Appl. No. 16/677,216.
Yasuda, et al., "Contact Angle of Water on Polymer Surfaces", Am Chem, Langmuir, vol. 10 No. 7, Jan. 1, 1994.
Office Action dated Oct. 18, 2023 for U.S. Appl. No. 17/473,864.

* cited by examiner

US 11,937,864 B2

ABLATION SYSTEMS WITH PARAMETER-BASED MODULATION AND RELATED DEVICES AND METHODS

RELATED APPLICATIONS

This application claims priority to U.S. Provisional Application No. 62/757,596, filed on Nov. 8, 2018 and titled "Tumor Ablation Device and Related Systems and Methods," and U.S. Provisional Application No. 62/757,578, filed on Nov. 8, 2018 and titled "Ablation Systems with Parameter-Based Modulation and Related Devices and Methods," both of which are incorporated herein by reference in their entireties.

TECHNICAL FIELD

The present disclosure relates generally to the field of medical devices. More particularly, some embodiments relate to tumor ablation devices and related systems and methods.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
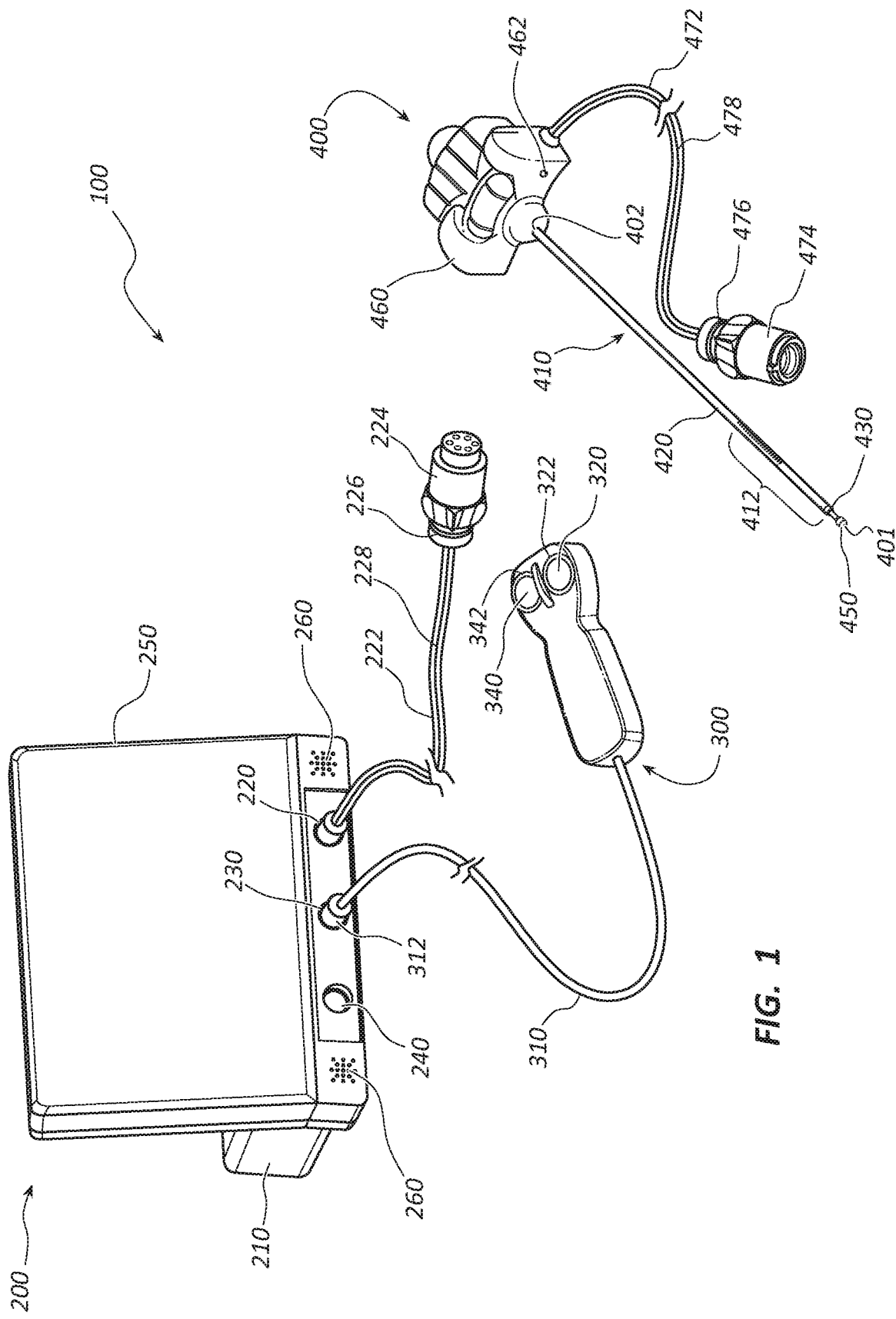
FIG. 1 is a perspective view of a tumor ablation system that includes a base unit, a remote, and a medical device.

Tumor ablation devices can be used to treat a tumor in a vertebra or other bones, such as the long bones of a patient. For example, in some embodiments, a distal end of a tumor ablation device may be inserted into a vertebra of a patient. Once the distal end of the tumor ablation device is inserted into the vertebra of the patient, an articulating distal portion of the tumor ablation device may be manipulated to position the tumor ablation device at a desired location within a tumor of the patient. The tumor ablation device may then be activated. Activation of the tumor ablation device may cause an electrical current (e.g., a radiofrequency current) to be applied to ablate tissue, such as the tumor. For instance, radiofrequency current may pass between a first electrode and a second electrode of the tumor ablation device. As the electrical current passes between the first electrode and the second electrode, the current may pass through tissue of the patient, thereby heating (and potentially killing) the adjacent tissue (e.g., tumor cells). The tumor ablation device may comprise one or more temperature sensors which may be used to measure the temperature of the heated tissue adjacent to the tumor ablation device. Based on the information obtained from impedance between the first electrode and the second electrode and/or from one or more temperature sensors, the duration, position, and/or magnitude of the delivered thermal energy may be tailored to ablate tumor tissue within a desired region of the tumor while avoiding the delivery of damaging amounts of thermal energy to healthy tissue. In some embodiments, once the tumor has been treated with thermal energy (e.g., converted radiofrequency energy), a cement may be delivered through with a different device to stabilize the vertebra of the patient.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities. Two components may be coupled to each other even though they are not in direct contact with each other. For example, two components may be coupled to one another through an intermediate component. The phrases "attached to" or "attached directly to" refer to interaction between two or more entities that are in direct contact with each other and/or are separated from each other only by a fastener of any suitable variety (e.g., an adhesive).

The terms "proximal" and "distal" are opposite directional terms. For example, the distal end of a device or component is the end of the component that is furthest from the practitioner during ordinary use. The proximal end refers to the opposite end, or the end nearest the practitioner during ordinary use.

FIG. 1 illustrates a tumor ablation system 100 for use in one or more medical procedures, such as procedures to treat a spinal tumor in one or more vertebral bodies of a patient. The tumor ablation system 100 however is not limited to treating spinal tumors in vertebral bodies, but may be used to treat tumors in various other locations in the body, such as a hip, pelvis, or other long bones. The tumor ablation system 100 may comprise a base unit 200, one or more medical devices 400 (or portions thereof) or medical device assemblies for use in a tumor ablation procedure, and a remote 300 that may enable a user to control energy delivery to the medical device 400, or other aspects of the medical device 400.

The base unit 200 may comprise a housing 210 that may house one or more power supplies (e.g., a radiofrequency ("RF") generator) that provides RF energy to a RF energy delivery probe 410 of the medical device 400. The base unit 200 may further comprise ports 220, 230, 240 that couple the medical devices 400 and the remote 300 to the base unit 200. The base unit 200 of FIG. 1 may include two power supplies (not shown) disposed in the housing 210. In the illustrated embodiment, one of the power supplies may correspond to port 220 and the other power supply may correspond to port 240. In other words, in some embodiments, each port 220, 240 may be electrically coupled to, and powered by, an independent power supply.

In some embodiments, the remote 300 may include a cable 310 and plug 312 that are configured to couple the remote 300 to the base unit 200 via port 230. This coupling may be configured to enable communication between the remote 300 and the base unit 200. In some embodiments, the port 230 may be a wireless port that wirelessly connects with the remote 300. The remote 300 may include a plurality of toggle buttons. The illustrated remote 300 of FIG. 1 illustrates two buttons 320 and 340. In the illustrated embodiment, toggle button 320 is configured to correspond with port 220 and a first power supply (RF generator) disposed in the housing 210 and button 340 is configured to correspond with port 240 and a second power supply (RF generator) disposed in the housing 210. Again, the two power supplies disposed in the housing 210 may be independent of each other. The toggle button 320 may thus be used toggle off and on the power supply (RF generator) corresponding to port 220 and thus toggle off and on energy delivery to a medical device coupled to port 220. Similarly, toggle button 340 may be configured to toggle off and on the delivery of energy to a medical device coupled to port 240.

Figure 5:
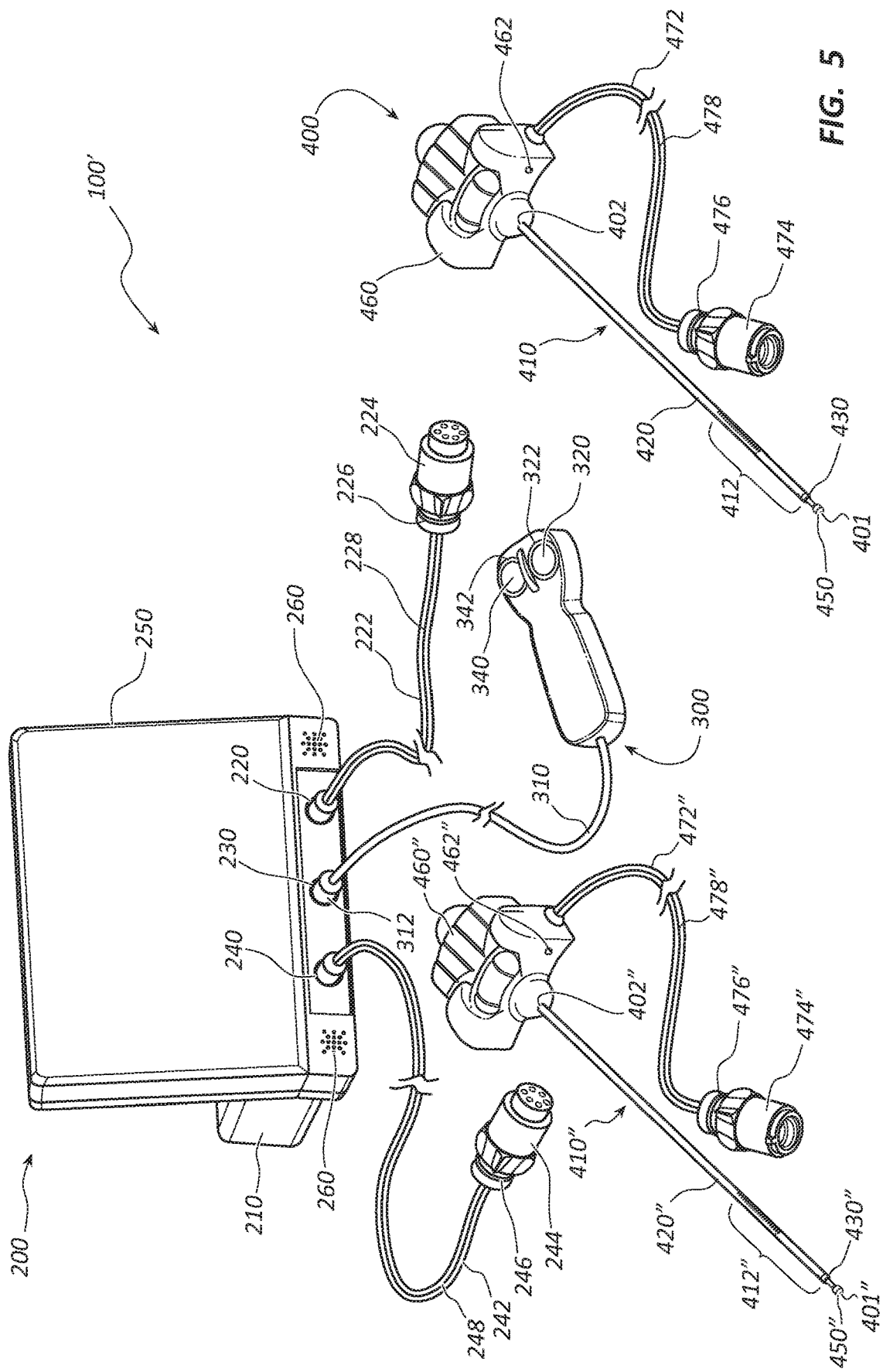
FIG. 5 is a perspective view of a tumor ablation system that includes a base unit, a remote, and a plurality of medical devices.

The tumor ablation system 100 may further include one or more medical devices 400 for performing a tissue ablation. FIG. 1 illustrates a single medical device 400 that may be used for single pedicle (unipedicular) vertebral access to treat a tumor or lesion. However, the tumor ablation system 100 may include more than one medical device 400. For example, FIG. 5 illustrates a tumor ablation system 100 with two medical devices 400 and 400' for performing a two pedicle (bipedicular) vertebral access to treat tumors or lesions.

The medical device 400 may further include a housing 460 and a cable 472 and plug 474 that is configured to couple the medical device 400 to the base unit 200 to enable communication between the medical device 400 and the base unit 200 and to provide electrical energy to the RF energy delivery probe 410. The base unit 200 may include an extension cable 222 and plug 224 that couples to port 220 or 240 and may extend the range of the RF energy delivery probe 410. In some embodiments, the cable and plug 474 may couple directly to port 220 or 240 without the use of the extension cable 222. As discussed above, each port 220 and 240 correspond with an independent power supply and medical device 400 may be coupled to either port 220 or 240 to access a power supply.

In the illustrated embodiment of FIG. 1, the tumor ablation system 100 is shown comprising a single medical device 400. The tumor ablation system 100 may include a plurality of identifying features that signify to a user which port (220 or 240) to which the medical device 400 is coupled. Systems within the scope of this disclosure may have any combination of the identifying features discussed below.

As detailed below, one or more portions of the medical device 400 or related components may have an indicator light or other feature that identifies the port (220 or 240) to which the medical device 400 is coupled. For example, the plug 474 may include a light 476 (e.g. LED) that lights up when the plug is coupled to either of the ports 220 and 240. For example, if the medical device 400 is coupled to port 220 the light 476 may light up a first color (e.g. blue). If the medical device 400 is coupled to port 240 the light 476 may light up a second color (e.g. white). The light 476 may be a ring that extends around the circumference of the plug 474.

Another identifying feature may be a light 478 (e.g. LED) disposed along the length of the cable 472. The light 478 of the cable 472 may light a first color (e.g. blue) when the medical device 400 is coupled to port 220 and may light up a second color (e.g. white) when the medical device 400 is coupled to port 240.

Similar identifying features may be disposed on the extension cable 222 and plug 224. For example, the plug 224 may include a light 226 (e.g. LED) that may light up a first color (e.g. blue) when the extension cable 222 and plug 224 are coupled to the port 220 and/or a medical device and may light up a second color (e.g. white) when the extension cable 222 and plug 224 are coupled to the port 240 and/or a medical device. The light 226 may be a ring that extends around the circumference of the plug 224. The cable 222 may include a light 228 that is disposed along the length of the extension cable 222 and the light 228 may light up a first color (e.g. blue) when cable 222 and plug 224 are coupled to the port 220 and/or a medical device and a second color (e.g. white) when the cable 222 and plug 224 are coupled to the port 240 and/or a medical device.

Another identifying feature may be a light 462 (e.g. LED) disposed on the housing 460 of the medical device 400. The light 462 of the housing 460 may light a first color (e.g. blue) when the medical device 400 is coupled to port 220 and may light up a second color (e.g. white) when the medical device 400 is coupled to port 240.

Another identifying feature may be disposed on the remote 300. The remote 300 may include lights that distinguish between which toggle button 320 and 340 correspond with each port 220 and 240. For example, toggle button 320 may include a light 322 (e.g. LED) that lights up a first color (e.g. blue) when the remote is coupled to or wirelessly connected to port 230. Toggle button 340 may include a light 342 (e.g. LED) that lights up a first color (e.g. white) when the remote 300 is coupled to or wirelessly connected to port 230. Unlike the other identifying features, the toggle buttons 320 and 340 do not alternate between colors but are color specific to the corresponding port. Accordingly, the user may always know which toggle button 320 and 340 corresponds to which port 220 and 240.

Again, the plurality of identifying features may be independent of the other identifying features or they may be in a number of different combinations. For example, in one embodiment, one of the lights 476, 478, 226, 228, and 462 may be used as the only identifying feature. In another embodiment, light 476 of the plug 474 may work in conjunction with the light 462 of the housing 460. A plurality of different combinations may be used in an attempt to help a physician identify which medical device is coupled to which port 220 and 240.

The base unit 200 may further include a plurality of speakers 260. The speakers 260 enable the base unit 200 to provide audible indicators to the user. For example, when a medical device is turned on and is coupled to port 220 and ablating, the base unit 200 may give a first audible indicator. If a second medical device is turned on and is coupled to port 240 and ablating, the base unit 200 may give a second audible indicator. The audible indicators are different from each other and the user would be able to know by sound if one or two medical devices are currently ablating.

Figure 2A:
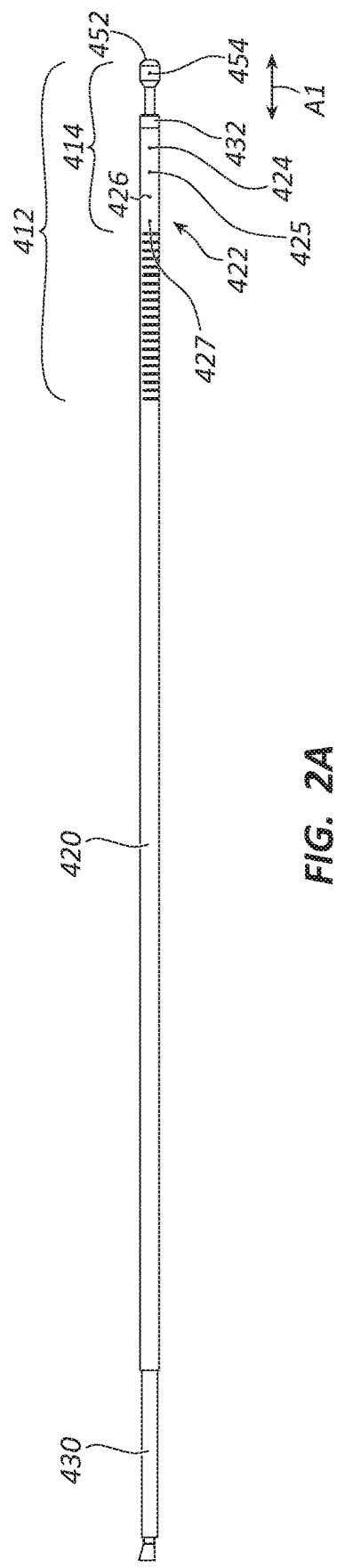
FIG. 2A is a side view of a RF (radiofrequency) energy delivery probe of the medical device of FIG. 1.
Figure 2B:
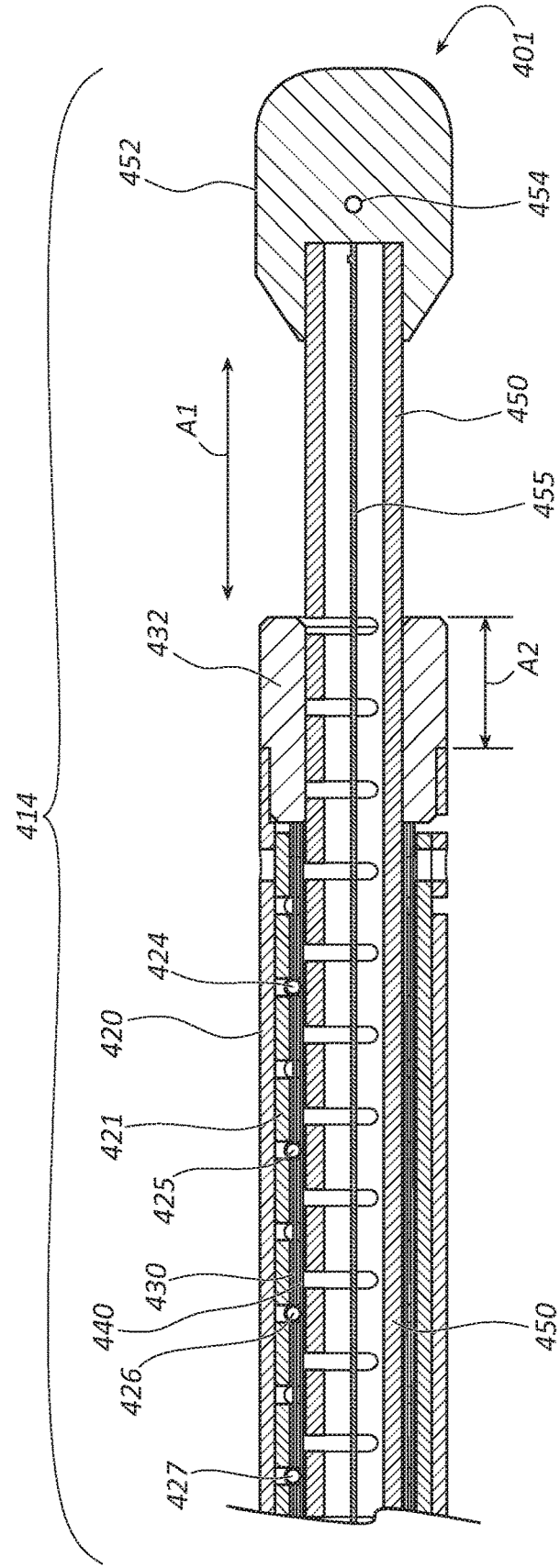
FIG. 2B is a cross-sectional view of the distal portion of the RF energy delivery probe of FIG. 2A.

FIGS. 2A-2B illustrate a probe of the medical device 400 in greater detail. FIG. 2A illustrates a side view of the RF energy delivery probe 410, and FIG. 2B illustrates a detailed cross-sectional view of the distal portion of the RF energy delivery probe 410. The RF energy delivery probe 410 may have a first pole or RF+ pole and a second pole, return pole, or RF− pole, the first tubular insulator 430, the second tubular insulator 440, and a primary insulator, or bushing insulator 432 that is disposed between the poles and may act as a bushing.

Though various elements of the embodiment of FIGS. 2A and 2B are referenced as "tubular" (e.g. the first tubular conductor 420, first tubular insulator 430, second tubular insulator 440, and second tubular conductor 450), other geometries of these elements are within the scope of this disclosure. That is, one or more of these elements may be configured with a non-tubular geometry in some embodiments. Further, tubular elements with various cross-sectional shapes, including round, square, rectangular, triangular, polygonal, and so forth are likewise within the scope of this disclosure. Additionally, tubular elements wherein the cross-sectional geometry or size varies along the length of the tubular element are within the scope of this disclosure.

The first tubular conductor 420 may be a metallic tube that extends from a proximal anchor (e.g., a metallic anchor) to an open distal end. The first tubular conductor 420 may act as the second pole (RF−). In some embodiments, a complimentary tubular conductor 421 may be disposed within the first tubular conductor 420. The complimentary tubular conductor may be metallic and may be physically and electrically connected to the first tubular conductor 420.

The first tubular insulator 430 may be at least partially disposed within the first tubular conductor 420. For example, the first tubular insulator 430 may extend through the first tubular conductor 420. More particularly, in some embodiments, the first tubular insulator 430 extends through the first tubular conductor 420 such that a proximal end of the first tubular insulator 430 is proximal of the first tubular conductor 420 and a distal end of the first tubular insulator 430 is proximal of the first tubular conductor 420. The first tubular insulator 430 and the second tubular insulator 440 may be made from any suitable insulating material, such as polymeric insulating materials. Examples of suitable polymeric insulating materials include polyimide, polycarbonate, polyetheretherketone (PEEK), and polyether block amides (e.g., PEBAX®). The first tubular insulator 430 may extend past the open of the first conductor 420 and may act as the primary insulator, or bushing insulator 432, e.g., bushing, between the first pole or RF+ pole and the second pole, return pole, or RF− pole. That is, the first tubular insulator 430 may extend a sufficient distance to function as an insulator along the portion of the exemplary embodiment where the bushing insulator 432 is disposed. In this way the first tubular insulator 430 may take the place of the bushing insulator 432, such that there is no separate element defining the bushing insulator 432. Additionally, in some embodiments, the first tubular insulator 430 may extend along the device and comprise an enlarged section that defines the bushing insulator 432. Thus, the first tubular insulator 430 and bushing insulator 432 may be a single part and may or may not have the same cross-sectional geometry and/or size. In other embodiments, the bushing insulator 432 may be a separate component from the first tubular insulator 430. In such a case, materials such as ceramics (Zirconia) may be considered.

The second tubular insulator 440 may be disposed within the first tubular insulator 430. For example, the second tubular insulator 440 may extend through the first tubular insulator 430. More particularly, in some embodiments, the second tubular insulator 440 extends through the first tubular insulator 430 such that a proximal end of the second tubular insulator 440 is proximal of the first tubular insulator 430 and a distal end of the second tubular insulator 440 is in line with the distal end of the first tubular insulator 430. The second tubular insulator 440 may be made from any suitable insulating material, such as polymeric insulating materials. Examples of suitable polymeric insulating materials include polyimide, polyetheretherketone (PEEK), and polyether block amides (e.g., PEBAX®). In some embodiments, the second tubular insulator 440 may act as the primary insulator or bushing insulator 432, e.g., bushing, between the first pole or RF+ pole and the second pole, return pole, or RF− pole. That is, as with the first tubular insulator 430, the second tubular insulator 440 may extend and form the bushing insulator 432 or may be a separate component from the bushing insulator 432.

The second tubular conductor 450 may be a metallic tube that extends from a proximal end (e.g., a metallic anchor) to a distal end. In some embodiments, the second tubular conductor 450 is rigid (or is rigid along most of its length). The second tubular conductor 450 may be at least partially disposed within the second tubular insulator 440. For example, the second tubular conductor 450 may extend through the second tubular insulator 440 such that a distal portion 452 of the second tubular conductor 450 is disposed distal of the first tubular conductor 420, the first tubular insulator 430, and the second tubular insulator 440. In some embodiments, the distal portion 452 of the second tubular conductor 450 that is disposed distal of the first tubular insulator 430 is longitudinally offset from the first tubular conductor 420 by the longitudinal length of the bushing insulator 432. The bushing insulator 432 may have a length A2 of between 0.1 cm and 0.5 cm. Stated differently, the gap between the distal portion 452 the second tubular conductor 450 and the distal end of the first tubular conductor 420 may be between 0.3 cm and 1.0 cm when the distal portion 452 is in a non-deployed or non-extended configuration, as further detailed below.

The distal portion 452 of the second tubular conductor 450 may act as the first probe electrode (RF+). The second tubular conductor 450 may extend and retract relative to the first tubular conductor 420. In some embodiments, the second tubular conductor 450 may extend and retract axially up to 8 mm, as shown by arrow A1. In some embodiments, the RF energy delivery probe 410 may extend and retract up to 5 mm. In some embodiments, the RF energy delivery probe 410 may extend and retract up to 1 mm. The axial movement of the RF energy delivery probe 410 may be controlled by the physician or by another medical professional and may be displayed on the display 250. The axial movement of the second tubular conductor 450 relative to the first tubular conductor 420 creates a continuous range of distances between the first tubular conductor 420 and the second tubular conductor 450. As discussed later, the extension and retraction of the second tubular conductor 450 relative to the first tubular conductor 420 affects the size of the ablation zones created by the RF energy delivery probe 410.

The RF energy delivery probe 410 may further comprise a plurality of thermocouples. In some embodiments, a distal thermocouple 454 may be disposed within the distal portion 452 of the second tubular conductor 450. The distal thermocouple 454 may be disposed near, or directly at, the maximum distal tip of the RF energy delivery probe 410 (meaning the distal-most point on the distal end 401 of the RF energy delivery probe 410). The distal thermocouple 454 may measure the temperature at the distal end 401 of the RF energy delivery probe 410. The temperature measured by the distal thermocouple 454 may be used for physician's reference and/or by a generator algorithm.

The RF energy delivery probe 410 may further comprise a plurality of thermocouples that are disposed proximal to the distal thermocouple 454. The illustrated embodiment of FIGS. 2A-2B illustrates four thermocouples that are proximal to the distal thermocouple 454. The thermocouples may be evenly spaced apart. A first proximal thermocouple 424 may be 5 mm back from the center of an ablation zone. A second proximal thermocouple 425 may be 10 mm back from the center of the ablation zone. A third proximal thermocouple 426 may be 15 mm back from the center of the ablation zone. A fourth proximal thermocouple 427 may be 20 mm back from the center of the ablation zone. In some embodiments, the fourth proximal thermocouple 427 may be 17.5 mm back from the center of the ablation zone. The thermocouples 424, 425, 426, 427 may be disposed between the first tubular insulator 430 and the second tubular insulator 440. Further, more or fewer thermocouples, positioned at different relative positions are also within the scope of this disclosure. For example, the thermocouples may be positioned at 5 mm intervals as described above or at 1 mm, 2 mm, 3 mm, 4 mm, or other intervals. Spacing wherein the offset between adjacent thermocouples is not constant along the plurality of thermocouples is also within the scope of this disclosure.

The temperatures measured by the proximal thermocouples 424, 425, 426, 427 and the temperature measured by the distal thermocouple 454 may be used for the physician's reference and/or may be employed by a generator algorithm. The algorithm may use the detected temperature to create symmetric ablation zones that reach a predetermined temperature or thermal dose to ablate or kill the targeted tumor or lesions. Thermal dose is a function of temperature and exposure time. For example, a thermal dose may vary the exposure time based on the temperature, and/or vary the temperature based on the exposure time. Thermal dose represents the accumulated thermal energy that the tissue in that location was subjected to during the total time of the procedure. In larger ablation sizes it takes much longer to reach a given temperature at the perimeter of the ablation zone than in smaller ablation zone sizes, and as a result a larger target ablation zone will be completed at a much lower temperature than a small ablation zone size (high temperature for a short time can deliver the same energy as low temperature for a long time). The thermal dose may allow better ablation size accuracy over a wide range of ablation sizes.

In some embodiments, the first tubular conductor 420 is rigid (or is rigid along most of its length). In some embodiments, a distal portion of the first tubular conductor 420 includes a plurality of slots 422 proximal to the open distal end and the proximal thermocouples 424, 425, 426, and 427. The proximal thermocouples 424, 425, 426, and 427 and the distal thermocouple 454 are disposed on a rigid and straight section 414 of the RF energy delivery probe 410. The rigid and straight section 414 may be configured to enable the RF energy delivery probe 410 to create symmetric ablation regions. The slots 422 may be perpendicular or angled relative to the primary axis of the first tubular conductor 420. In other embodiments, the first tubular conductor 420 lacks a plurality of slots 422. Other geometries of the slots 422 not specifically described herein fall within the scope of the disclosure.

The slots 422 may enable the distal portion 412 of the RF energy delivery probe 410 to articulate. In some instances, articulation of the distal portion 412 of the RF energy delivery probe 410 may facilitate placement of the distal portion 412 of the RF energy delivery probe 410 at a desired location for ablation. Stated differently, the RF energy delivery probe 410 may have an active steering capability that enables navigation to and within a tumor. In some instances, articulation of the distal portion 412 of the RF energy delivery probe 410 may, additionally or alternatively, mechanically displace tissue (e.g., tumor cells) within the vertebra of the patient. For example, the RF energy delivery probe 410 may function as an articulating osteotome that enables site-specific cavity creation. Stated differently, the articulating distal portion 412 of the RF energy delivery probe 410 may be robust enough to facilitate navigation through hard tissue of a patient. The practitioner may be able to articulate a distal portion 412 of the RF energy delivery probe 410 such that the distal portion 412 transitions from a linear configuration to a non-linear configuration. Articulation of the distal portion 412 may be similar to articulation of the medical device described in U.S. patent application Ser. No. 15/822,864, filed Nov. 27, 2017, hereby incorporated by reference in its entirety.

In some embodiments, the articulation of the RF energy delivery probe 410 may be displayed on the display 250.

Accordingly, the user may be able to see the extent of articulation during the procedure.

Figure 2C:
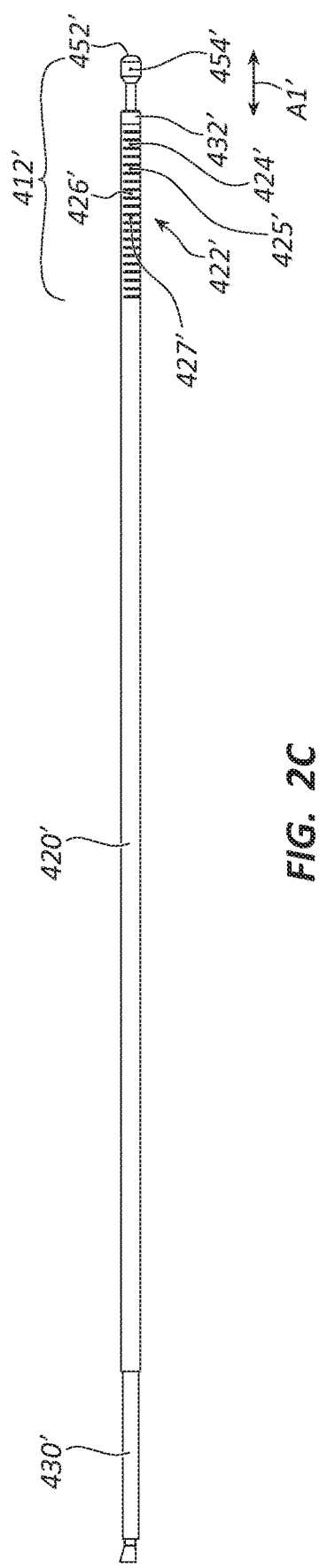
FIG. 2C is a side view of a RF (radiofrequency) energy delivery probe according to another embodiment.
Figure 2D:
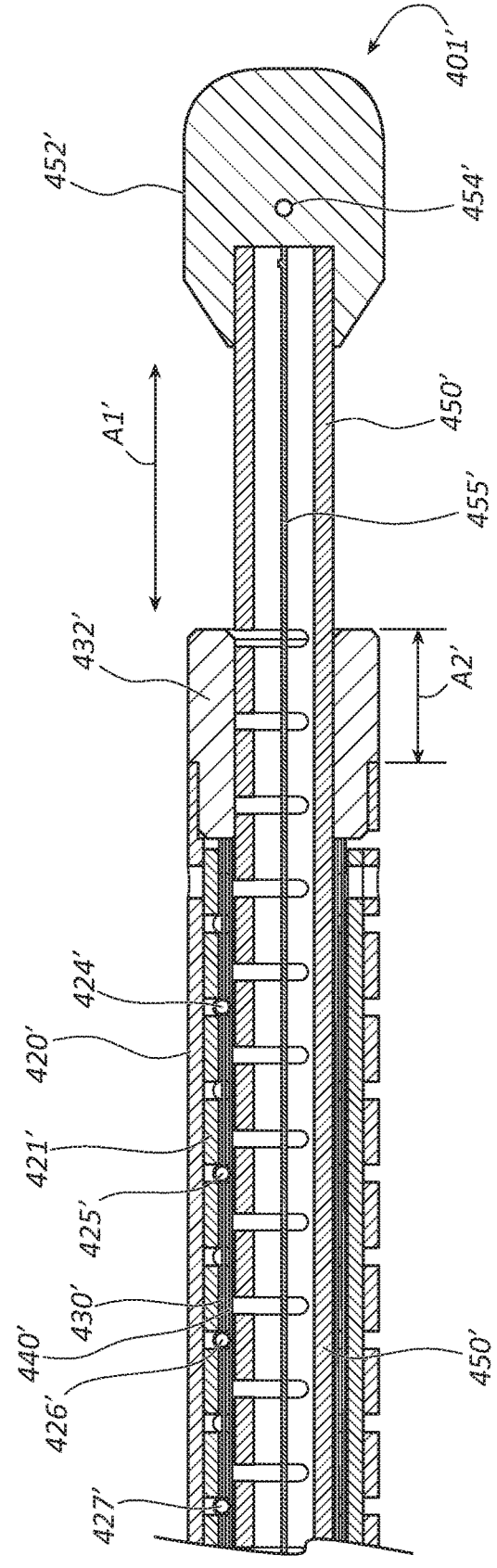
FIG. 2D is a cross-sectional view of the distal portion of the RF energy delivery probe of FIG. 2C.

FIGS. 2C-2D illustrate an alternative embodiment of the RF energy delivery probe 410' that include an articulating portion with a plurality of slots 422' that are adjacent to the open distal end and that corresponds with the proximal thermocouples 424', 425', 426', and 427'. The location of the articulating portion enables the RF energy delivery probe 410' to create a variety of different of ablation regions for ablating tumors.

FIGS. 3A-3D schematically illustrate a series of symmetric ablation zones 500a created by a RF energy delivery probe 410a. The symmetric ablation zones are symmetric about the poles of the first conductor 420 and the second conductor 450. The symmetric ablation zones 500a are three-dimensional, even though the FIGS. 3A-3D illustrate them as two-dimensional. As compared with the RF energy delivery probe 410 of FIGS. 1-2B, FIGS. 3A-3D illustrate variation on the design of the geometry of the distal tip of the RF energy delivery probe 410, thus the reference numerals in these figures are designated with a final letter "a" to indicate the variation with the prior embodiment. Nonetheless, disclosure related in connection with the embodiment of FIGS. 1-2B may be applied to the embodiment of FIGS. 3A-3D and vice versa. In the embodiment of FIGS. 3A-3D, a distal thermocouple 454a and proximal thermocouples 424a, 425a, 426a, 427a are shown in each of FIGS. 3A-3D.

Figure 3A:
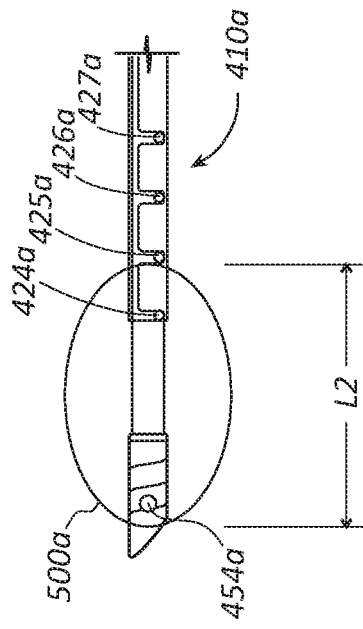
FIG. 3A is a schematic representation of a first exemplary ablation zone created by a RF energy delivery probe.
Figure 3B:
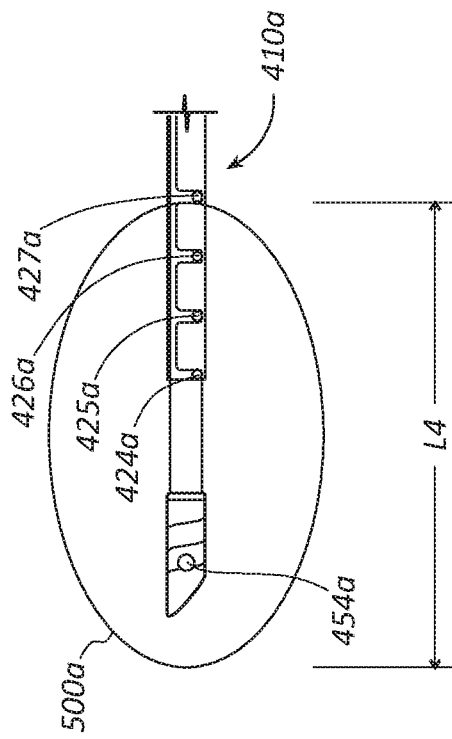
FIG. 3B is a schematic representation of a second exemplary ablation zone created by the RF energy delivery probe of FIG. 3A.
Figure 3C:
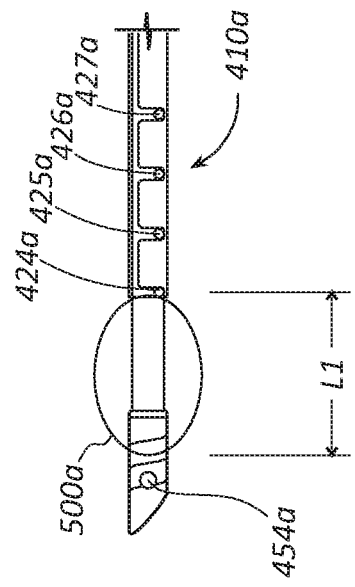
FIG. 3C is a schematic representation of a third exemplary ablation zone created by the RF energy delivery probe of FIG. 3A.
Figure 3D:
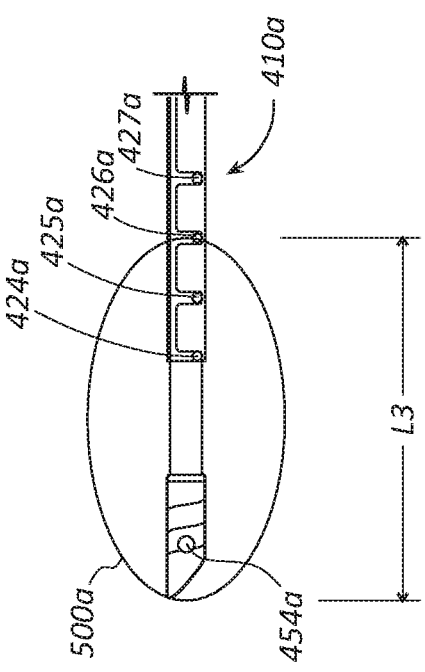
FIG. 3D is a schematic representation of a fourth exemplary ablation zone created by the RF energy delivery probe of FIG. 3A.

FIG. 3A illustrates a first ablation zone 500a with a length L1. In some embodiments, the length of L1 is 1 cm. FIG. 3B illustrates a second configuration where the ablation zone 500a has a length L2. In some embodiments, the length of L2 is 2 cm. FIG. 3C illustrates a third configuration where the ablation zone 500a has a length L3. In some embodiments, the length of L3 is 3 cm. FIG. 3D illustrates a fourth configuration where the ablation zone 500a has a length L4. In some embodiments, the length of L4 is 4 cm. In other embodiments, the length of L4 is 3.5 cm. While the present disclosure contemplates multiple ablation zone sizes, the present disclosure is not limited to these proposed ablation zone sizes. In fact, multiple ablation zone sizes are within the scope of these disclosure based on a single probe design.

The size of the ablation zone 500a may be controlled by modulating the delivery of electrical energy, such as radiofrequency energy, to the RF energy delivery probe 410a. In the illustrated embodiment, correlation between a 5 mm offset proximal thermocouples, 424a, 425a, 426a, and 427a, and 1 cm increments of the ablation zone size (due to 5 mm growth of the ablation zone 500a on each side of the distal tip of the RF energy delivery probe 410a) is shown. Again, in other embodiments, different sizes of ablation zone, including different increments for controlling the ablation zone 500a size, and different placement of the proximal thermocouples 424a, 425a, 426a, and 427a may be used.

The medical device may be configured to create symmetric ablation zones even when the RF energy delivery probe 410a is articulated along a distal portion (such as distal portion 412 of FIG. 1) because of the rigid and straight portion 414 where the thermocouples 424, 425, 426, and 427 are disposed.

Figures 4A, 4B, 4C:
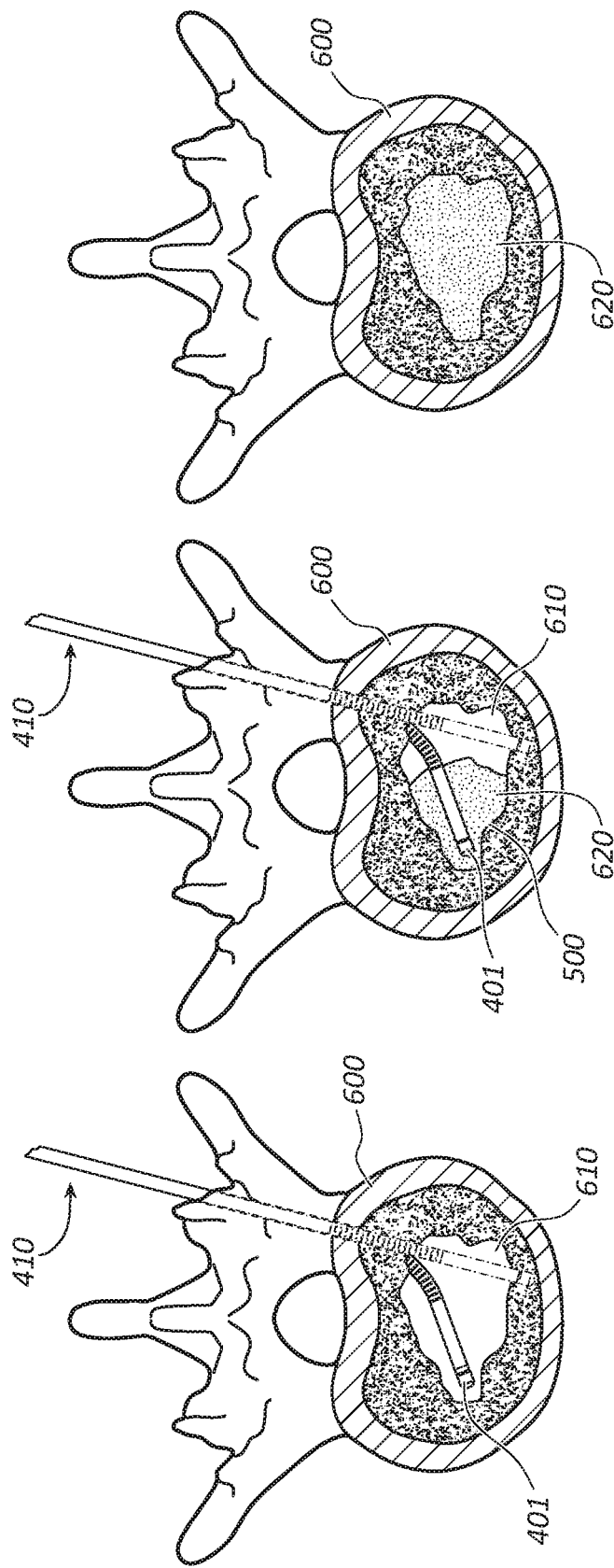
FIG. 4A is a schematic representation of the RF energy delivery probe of FIG. 1 being inserted into a vertebral body of a patient to treat a tumor or lesion using uni-pediclular vertebral access.
FIG. 4B is a schematic representation of the RF energy delivery probe of FIG. 1 delivering energy to ablate the tumor or lesion shown with a portion of the tumor or lesion ablated.
FIG. 4C is a schematic representation of dead tissue of the ablated tumor or lesion with the RF energy delivery probe removed from the vertebral body.

FIGS. 4A-4C illustrate a method for treating a spinal tumor or lesion 610 in one or more vertebral bodies 600 of a patient using the medical device 400 of FIG. 1 by unipedicular access. For example, some embodiments of a medical procedure may comprise obtaining the medical device (400 of FIG. 1) and inserting the distal end 401 of the RF energy delivery probe 410 into a vertebral body of a patient (e.g., a sedated patient in the prone position). In some embodiments, the distal end 401 of the RF energy delivery probe 410 may be pointed and the pointed distal end 401 may facilitate penetration of bone within the vertebra of the patient. Further, in some embodiments, the RF energy delivery probe 410 has sufficient strength to prevent buckling of the RF energy delivery probe 410 as the distal end of the RF energy delivery probe 410 is inserted within a vertebra (e.g., across the cortical bone) of the patient. In some embodiments, the distal end 401 of the RF energy delivery probe 410 is inserted into the patient via an introducer (not shown). In other embodiments, the distal end 401 of the RF energy delivery probe 410 may be inserted into the soft tissue of the patient without using an introducer.

FIG. 4A illustrates the RF energy delivery probe 410 inserted into the vertebra 600 of a patient with the tumor 610. The distal portion (412 of FIG. 1) of the RF energy delivery probe 410 may be articulated to place the RF energy delivery probe 410 in a predetermined position. The RF energy delivery probe 410 may be activated and the RF generator may provide energy for the RF energy delivery probe 410 to ablate the tumor 610. The RF energy delivery probe 410 may then create a symmetric ablation zone 500 (similar to the ablation zones 500a discussed in connection with FIGS. 3A-3D). With reference to FIG. 1 and FIGS. 2A-2B, the distal thermocouple 454 and the proximal thermocouples 424, 425, 426, 427 may detect the temperature of the surrounding tissue and provide the temperature feedback to the base unit 200, which may be displayed on the display 250. This information may then be fed into the generator algorithm to maintain a symmetric ablation zone to ablate the tumor 610 and avoid damaging surrounding tissue.

FIG. 4B illustrates ablated tissue 620 of the tumor 610 as the tissue reaches a predetermined temperature such as 60 degrees Celsius, or thermal dose. Once the tumor 610 reaches the predetermined temperature or thermal dose, the RF generator may turn off the power, or otherwise modify current delivery to the RF energy delivery probe 410. The diameter of the ablation zone 500 may be determined based on the size of the tumor 610. If the tumor 610 is smaller, the ablation zone 500 may be smaller and a subset of the proximal thermocouples 424, 425, 426, 427 may be used to detect the temperature in and immediately adjacent the ablation zone 500. If the ablation zone 500 is larger, all of the proximal thermocouples 424, 425, 426, 427 may be used to detect the temperature within and adjacent the ablation zone 500. That is to say, while all the proximal thermocouples 424, 425, 426, and 427 may monitor temperature and provide feedback to the base unit 200, in some procedures, only a subset of the proximal thermocouples 424, 425, 426, and 427 may be within and/or immediately adjacent the ablation zone 500. FIG. 4C illustrates the dead tissue 620 of the ablated tumor 610 with the RF energy delivery probe 410 removed from the vertebra 600 of the patient.

As discussed previously, FIG. 5 illustrates a tumor ablation system 100' with two medical devices 400 and 400" for performing a bipedicular vertebral access to treat tumors. In the illustrated embodiment, the tumor ablation system 100' comprises the base unit 200, remote 300, and medical device 400 of the tumor ablation system 100 of FIG. 1. That is to say, a tumor ablation system may be configured with a single medical device 400 or two medical devices 400 and 400", depending on the desired treatment. For clarity with connecting the disclosure of the tumor ablation system 100 and the tumor ablation system 100' the tumor ablation system 100', is shown as comprising the noted elements of the tumor ablation system 100. Embodiments wherein elements such as the base unit 200 and remote 300 are configured for use with only one, with one or two, with only two, or with other numbers of medical devices 400, 400' are likewise within the scope of this disclosure.

The second medical device, medical device 400", may be similar to the first medical device, medical device 400, or may be different based on treatment needs of the patient. The remote 300 may allow the user to adjust the energy provided to each medical device 400 and 400". In some embodiments, energy adjustment may be done automatically via an algorithm. For example, the remote 300 may have a button 320 for controlling the amount of energy to the medical device 400, 400" plugged into port 220 and a button 340 for controlling the amount of energy to the medical device 400, 400" plugged into port 240.

As discussed above, each medical device 400 and 400" may include a plurality of identifying features to help identify which medical device 400 and 400" is coupled to which port 220 and 240.

Figure 6:
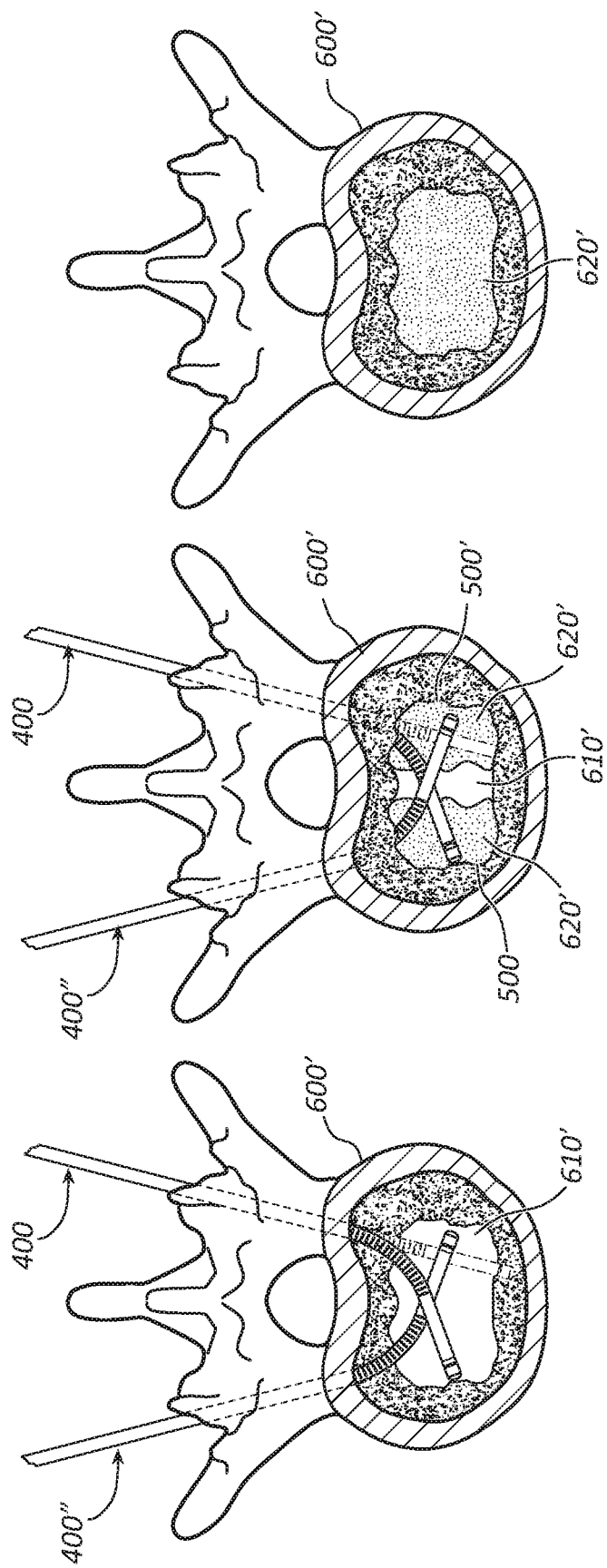
FIG. 6A is a schematic representation of two RF energy delivery probes being inserted into a vertebral body of a patient to treat a tumor or lesion using bi-pedicle vertebral access.
FIG. 6B is a schematic representation of two RF energy delivery probes delivering energy to ablate the tumor or lesion with a portion of the tumor or lesion ablated.
FIG. 6C is a schematic representation of dead tissue of the ablated tumor or lesion with two RF energy delivery probes removed from the vertebral body.

FIGS. 6A-6C illustrate a method for treating a spinal tumor 610' in one or more vertebral bodies 600' of a patient using the medical devices 400 and 400" using bipedicular access. For example, some embodiments of a medical procedure may involve obtaining the medical devices 400 and 400" and inserting the distal ends 401 and 401" of the RF energy delivery probes 410, 410" into a vertebral body of a patient (e.g., a sedated patient in the prone position). In other embodiments, the distal end 412 and 412" of the first tubular conductor 420 may be inserted into a vertebral body of the patient. In some embodiments, the distal ends 401 and 401" of the RF energy delivery probes 410, 410" or the distal end 412 and 412" of the first tubular conductor 420 may be pointed and the pointed distal ends may facilitate penetration of bone within the vertebra 600' of the patient. In some embodiments, the RF energy delivery probes 410, 410" have sufficient strength to prevent buckling of the RF energy delivery probes 410, 410" as the distal ends 401 and 401" of the RF energy delivery probes 410, 410" are inserted within the vertebra 600' (e.g., across the cortical bone) of the patient. In some embodiments, the distal ends 401 and 401" of the RF energy delivery probes 410, 410" are inserted into the patient via an introducer (not shown). In other embodiments, the distal ends 401 and 401" of the RF energy delivery probes 410, 410" are inserted into the patient without using an introducer.

FIG. 6A illustrates the medical devices 400 and 400" inserted into a vertebra 600' of a patient with a tumor 610'. The distal portions 412 and 412" of the RF energy delivery probes 410 and 410" may be articulated to place the RF energy delivery probes 410 and 410" in predetermined positions. The RF energy delivery probes 410 and 410" may be activated and the RF generator may provide energy to the RF energy delivery probes 410 and 410" to ablate the tumor 610'. The RF energy delivery probes 410 and 410" may each create symmetric ablation zones 500, 500', similar to the ablation zones 500 discussed in FIGS. 3A-3D. The distal thermocouples 454 and 454" and the proximal thermocouples 424, 425, 426, 427, 424', 425", 426", and 427" may detect the temperature of the surrounding tissue and provide the temperature feedback to the base unit 200, which may be displayed on the display 250. This information may be fed into the generator algorithm to maintain a symmetric ablation zone 500, 500' to ablate the tumor 610' and avoid damaging surrounding tissue.

FIG. 6B illustrates the ablated tissue 620' of the tumor 610' as the tissue reaches a predetermined thermal dose or temperature, such as 60 degrees Celsius. Once the tumor 610' reaches the predetermined temperature or thermal dose, the RF generator may turn off the power, or otherwise modify current delivery to the RF energy delivery probes 410 and 410'. The diameter of the ablation zones 500, 500' may be determined based on the size of the tumor 610'. If the tumor 610' is smaller, the ablation zones 500, 500' may be smaller and only a subset of the proximal thermocouples 424, 425, 426, 427, 424", 425", 426", and 427" may be used to detect the temperature in and immediately adjacent the ablation zones 500, 500', as also described above in connection with FIG. 4B. FIG. 6C illustrates the dead tissue 620' of the ablated tumor 610' with the RF energy delivery probes 410 and 410' removed from the vertebra 600' of the patient.

Figure 7:
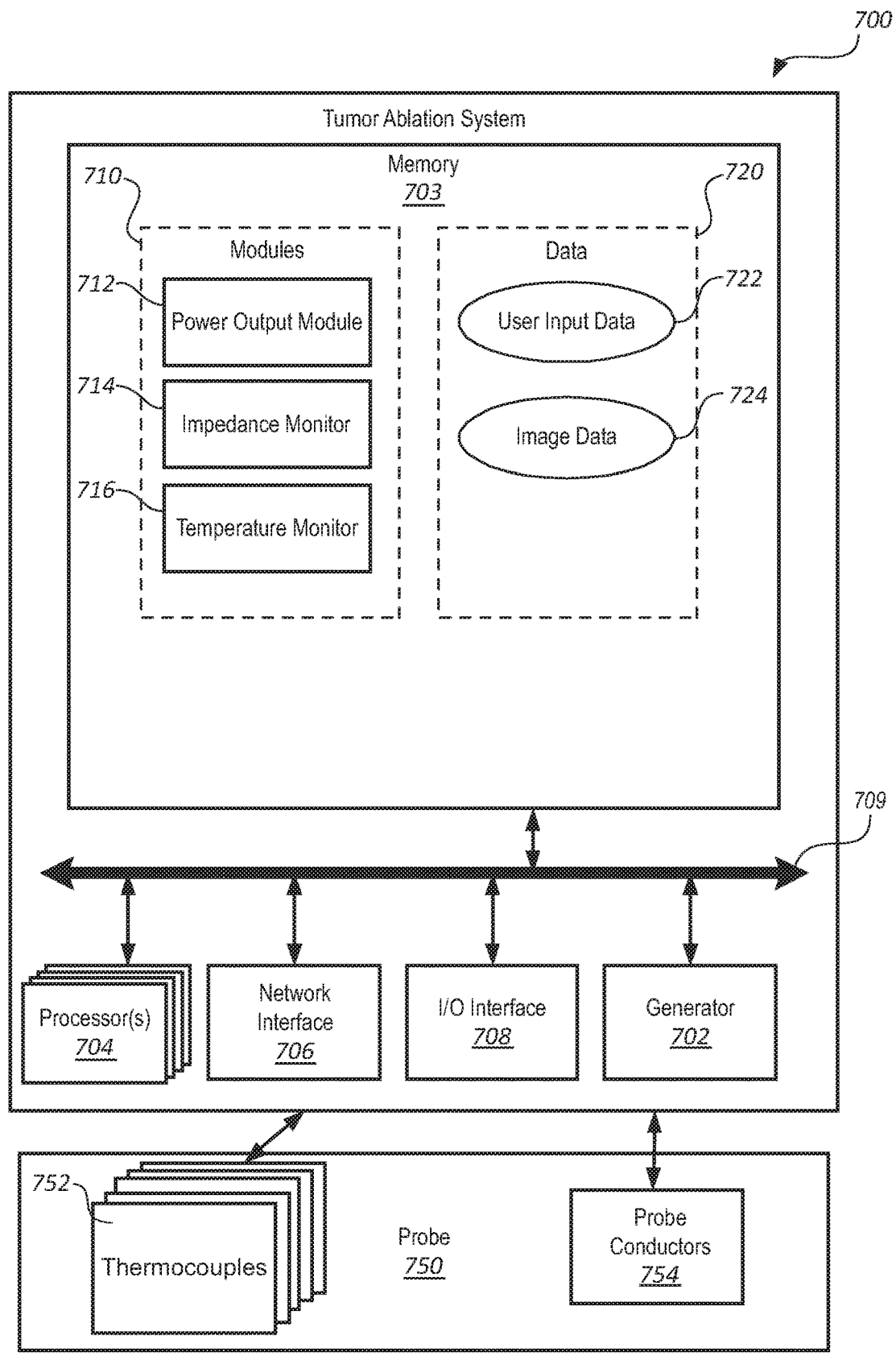
FIG. 7 is a block diagram of a tumor ablation system in communication with a probe according to one embodiment.

FIG. 7 is a block diagram of a tumor ablation system 700 in communication with a probe 750 according to one embodiment. The tumor ablation system 700 may be the same tumor ablation system 100 illustrated in the previous figures. The tumor ablation system 700 includes a generator 702 that can produce an electrical current to output to the probe 750. In some embodiments, the tumor ablation system 700 may drive two probes with two independent generators. The electrical current can be conducted between a first conductor and a second conductor (probe conductors 754) as radio frequency (RF) energy is converted into thermal energy via tissue heating within a desired ablation region. The tumor ablation system 700 modulates power output based on temperature and impedance of tissue surrounding the probe 750.

In some embodiments, the probe 750 comprises a first conductor at a proximal portion of the probe 750 and a second conductor nearer a distal portion than the first conductor. An insulator separates the first conductor and the second conductor. The tissue within the desired ablation region provides a conduit through which the electrical current is conducted from the first conductor to the second conductor.

The probe 750 further comprises a set of thermocouples 752. In some embodiments, a first thermocouple is positioned to measure a temperature at a location on the first conductor. In some embodiments, the thermocouples 752 include a second thermocouple, a third thermocouple, and a fourth thermocouple on the first conductor. Each thermocouple on the second conductor may define a point along potential ablation zone perimeters. In some embodiments, the thermocouples 752 include a distal thermocouple on the second conductor.

The tumor ablation system 700 can include a memory 703, one or more processors 704, a network interface 706, an input/output interface 708, and a system bus 709.

The one or more processors 704 may include one or more general purpose devices, such as an Intel®, AMD®, or other standard microprocessor. The one or more processors 704 may include a special purpose processing device, such as ASIC, SoC, SiP, FPGA, PAL, PLA, FPLA, PLD, or other customized or programmable device. The one or more processors 704 can perform distributed (e.g., parallel) processing to execute or otherwise implement functionalities of the presently disclosed embodiments. The one or more processors 704 may run a standard operating system and perform standard operating system functions. It is recognized that any standard operating systems may be used, such as, for example, Microsoft® Windows®, Apple® MacOS®, Disk Operating System (DOS), UNIX, IRJX, Solaris, SunOS, FreeBSD, Linux®, ffiM® OS/2® operating systems, and so forth.

The memory 703 may include static RAM, dynamic RAM, flash memory, one or more flip-flops, ROM, CD-ROM, DVD, disk, tape, or magnetic, optical, or other computer storage medium. The memory 703 may include a plurality of program modules 710 and program data 720. The memory 703 may be local to the tumor ablation system 700, as shown, or may be distributed and/or remote relative to the tumor ablation system 700.

The program modules 710 may include all or portions of other elements of the tumor ablation system 700. The program modules 710 may run multiple operations concurrently or in parallel by or on the one or more processors 704. In some embodiments, portions of the disclosed modules, components, and/or facilities are embodied as executable instructions embodied in hardware or in firmware, or stored on a non-transitory, machine-readable storage medium. The instructions may comprise computer program code that, when executed by a processor and/or computing device, cause a computing system to implement certain processing steps, procedures, and/or operations, as disclosed herein. The modules, components, and/or facilities disclosed herein may be implemented and/or embodied as a driver, a library, an interface, an API, FPGA configuration data, firmware (e.g., stored on an EEPROM), and/or the like. In some embodiments, portions of the modules, components, and/or facilities disclosed herein are embodied as machine components, such as general and/or application-specific devices, including, but not limited to: circuits, integrated circuits, processing components, interface components, hardware controller(s), storage controller(s), programmable hardware, FPGAs, ASICs, and/or the like. Accordingly, the modules disclosed herein may be referred to as controllers, layers, services, engines, facilities, drivers, circuits, subsystems and/or the like.

The modules 710 may comprise a power output module 712, an impedance monitor 714, and a temperature monitor 716. The power output module 712 determines a primary thermocouple by determining which of the multiple thermocouples is nearest an outer perimeter of the desired ablation region. The power output module 712 adjusts an output current of the generator 702. For example, the power output module 712 may receive impedance measurements of the tissue around the probe 750 from the impedance monitor 714. The power output module 712 may cause the generator 702 to decrease the output power when the impedance increases or when a maximum distal temperature is reached. The maximum distal temperature is the hottest reading that a distal thermocouple measures before the tumor ablation system 700 decreases output power. In some embodiments, the power output module 712 may increase power output if the impedance does not increase.

In some embodiments, the power output module 712 may control the output current of the generator 702 based on a thermal energy set point or temperature set point. The power output module 712 also causes the generator 702 to stop the output current when a temperature measurement or thermal energy (temperature and time), received by the temperature monitor 716, at the primary thermocouple reaches a target threshold. In some embodiments, the temperature of a distal thermocouple is also used to control the generator power output.

In some embodiments power output module 712 may control the output current of the generator 702 based on the procedure. For example, the user may input the therapy type to be administered, and the power output module 712 may control the output current of the generator 702 based on a profile associated with that therapy type.

The power output module 712 can also control the generator power output based on user input data 722. In some embodiments, the user input data 722 can include a target temperature threshold, a thermal dose, a target time at the target temperature threshold, a target output power, or other user-defined parameters. For example, the tumor ablation system 700 can receive manual ablation input from a user to selectively override impedance-based control of the generator 702.

The memory 703 may also include the data 720. Data generated by the tumor ablation system 700, such as by the program modules 710 or other modules, may be stored on the memory 703, for example, as stored program data 720. The data 720 may be organized as one or more databases.

The data 720 may include user input data 722 and image data 724. The user input data 722 may include a target temperature threshold, a thermal dose, a target time at the target temperature threshold, a target output power, or other user-defined parameters. The image data 724 may include an image of the tissue. For example, the image may be a magnetic resonance imaging scan.

The input/output interface 708 may facilitate user interaction with one or more input devices and/or one or more output devices. The input device(s) may include a keyboard, mouse, touchscreen, light pen, tablet, microphone, sensor, or other hardware with accompanying firmware and/or software. The output device(s) may include a monitor or other display, printer, speech or text synthesizer, switch, signal line, or other hardware with accompanying firmware and/or software. For example, in one embodiment, the input/output interface 708 comprises a display to provide a graphical user interface illustrating the potential ablation perimeters. The input/output interface 708 can receive size input from a user to specify which of the potential ablation perimeters is to be used to define the desired ablation region. In some embodiments, the input/output interface 708 is a touchscreen, and the size input is received via the touchscreen. In some embodiments, the input/output interface 708 can superimpose one or more of the potential ablation perimeters on an image of the tissue.

In some embodiments, the tumor ablation system 700 includes an indicator light on each generator port, and the probe 750 also includes an indicator light. The tumor ablation system 700 may cause the indicator light on a port attached to the probe 750 to change colors to match the indicator light on the probe 750 to provide the user a visual indicator of the port providing power to the probe 750.

The network interface 706 may facilitate communication with other computing devices and/or networks and/or other computing and/or communications networks. The network interface 706 may be equipped with conventional network connectivity, such as, for example, Ethernet (IEEE 1102.3), Token Ring (IEEE 1102.5), Fiber Distributed Datalink Interface (FDDI), or Asynchronous Transfer Mode (ATM). Further, the network interface 706 may be configured to support a variety of network protocols such as, for example, Internet Protocol (IP), Transfer Control Protocol (TCP), Network File System over UDP/TCP, Server Message Block (SMB), Microsoft® Common Internet File System (CIFS), Hypertext Transfer Protocols (HTTP), Direct Access File System (DAFS), File Transfer Protocol (FTP), Real-Time Publish Subscribe (RTPS), Open Systems Interconnection (OSI) protocols, Simple Mail Transfer Protocol (SMTP), Secure Shell (SSH), Secure Socket Layer (SSL), and so forth.

The system bus 709 may facilitate communication and/or interaction between the other components of the system 700, including the one or more processors 704, the memory 703, the input/output interface 708, and the network interface 706.

FIGS. 8-12 illustrate a graphical user interface that may be displayed by the tumor ablation system 700 of FIG. 7.

Figure 8:
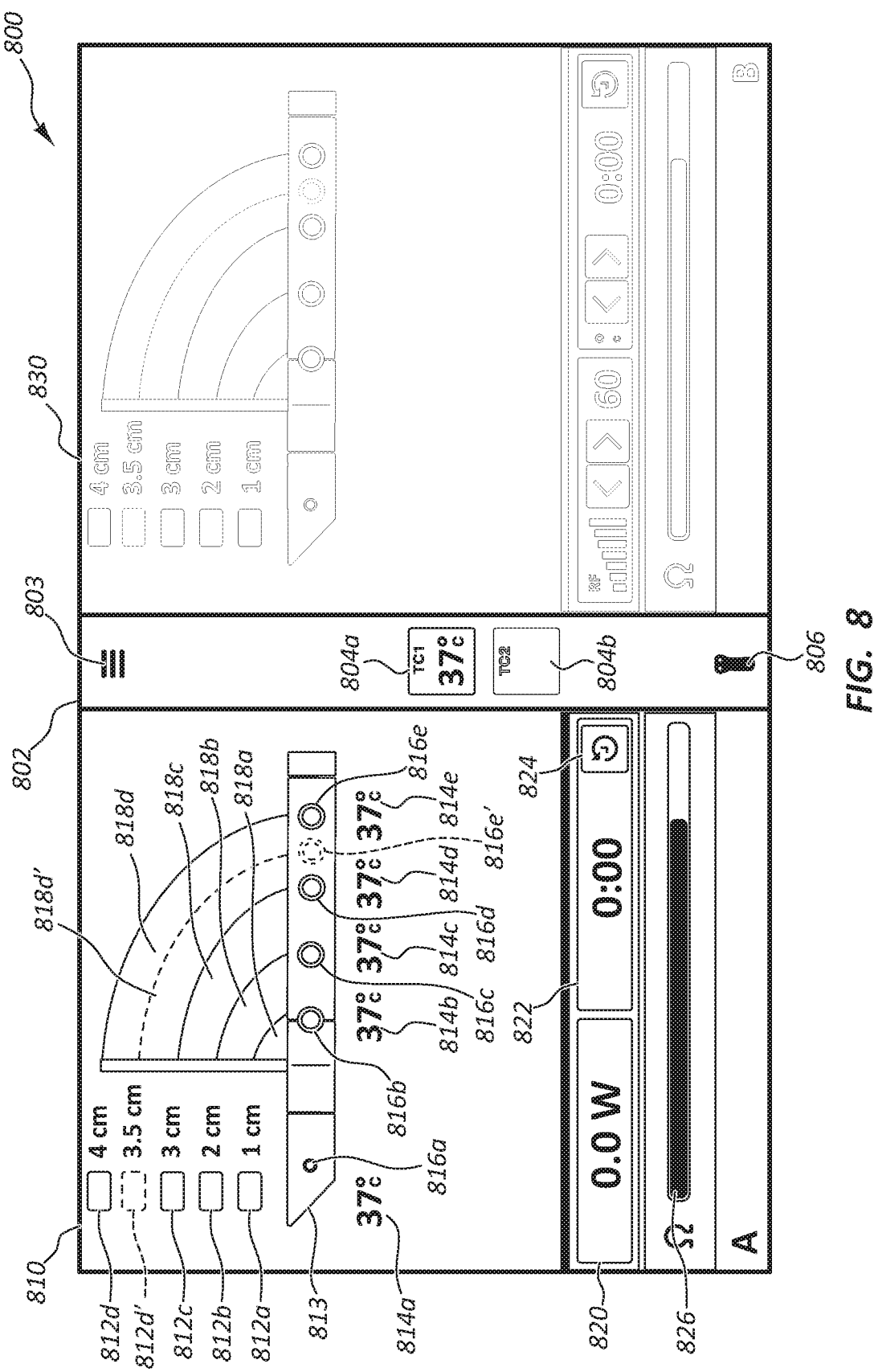
FIG. 8 is an interface to control a tumor ablation system with a generator coupled to a single probe, according to one embodiment.

Specifically, FIG. 8 is an interface 800 to control a tumor ablation system (e.g., the tumor ablation system 700 of FIG. 7) with a generator coupled to a single probe, according to one embodiment. The interface 800 enables configuration of parameters, setting of preferences, and the like for a tumor ablation procedure. Additionally, the interface 800 displays a current state of the tumor ablation procedure.

In the illustrated embodiment, the interface 800 includes a center configuration bar 802 dividing the interface 800 into two subinterfaces (i.e., probe A interface 810, probe B interface 830). The center configuration bar 802 includes a menu button 803, a first temperature measurement point informational element 804a, a second measurement point informational element 804b, and a remote informational element 806. The menu button 803 allows a user to open a settings menu. The first measurement point informational element 804a and the second measurement point information element display temperature measurements from two optional stand-alone remote thermocouple that the physician can place for additional thermal data. The remote informational element 806 indicates a status of a remote controller (e.g., coupled, uncoupled, error).

Each subinterface facilitates control of a probe and allows a user to monitor conditions associated with the probe. For example, the probe A interface 810 allows a user to control and monitor a probe coupled to the first port. The probe B interface 830 allows a user to control and monitor a probe coupled to the second port.

The probe A interface 810 includes a first zone input 812a, a second zone input 812b, a third zone input 812c, and a fourth zone input 812d, collectively referred to herein as zone inputs 812. The zone inputs 812 allow the user to control area size of an ablation zone. For example, if the user selects the first zone input 812a, the ablation zone will have a length of 1 centimeter. In some embodiments, the user may control the zone inputs 812 through a touchscreen interface. In some embodiments, the user may select a desired zone input via a curser. In some embodiments, the zone inputs 812 may correspond to physical buttons that a user may select to control the zone inputs 812.

The probe A interface 810 also includes a visual representation of a probe 813 coupled to port A. As illustrated, the probe 813 includes an illustration of a distal thermocouple 816a, a first proximal thermocouple 816b, a second proximal thermocouple 816c, a third proximal thermocouple 816d, and a fourth proximal thermocouple 816e, collectively referred to herein as thermocouples 816. Each of the thermocouples 816 is associated with a temperature measurement (i.e., first temperature measurement 814a, second temperature measurement 814b, third temperature measurement 814c, fourth temperature measurement 814d, and fifth temperature measurement 814e, collectively referred to herein as temperature measurements 814). The temperature measurements 814 display the temperature measurements from the thermocouples 816. In some embodiments, the temperature measurements 814 display a live temperature measurement from each of the thermocouples.

The probe A interface 810 also includes a visual representation of potential ablation zones (i.e., a first ablation zone 818a, a second ablation zone 818b, a third ablation zone 818c, and a fourth ablation zone 818d, collectively referred to herein as ablation zones 818). In the illustrated embodiment, the potential ablation zones 818 only display a quarter of an actual ablation area. However, the remainder of the actual ablation area may be assumed to be symmetric.

Each of the ablation zones 818 has a boundary point defined by one of the thermocouples 816. The ablation zones 818 may display for a user the current state of the tissue (e.g., ablated tissue, non-ablated tissue). In some embodiments, the ablation zones 818 are superimposed on an image of the tissue (e.g., MRI image). In some embodiments, the ablation zones that are selectable to the user may be limited based on the distance between the second tubular conductor 450 and to the first tubular conductor 420 because the distance affects the size of the ablation zones.

In some embodiments, the interface 800 includes a visual representation of fifth ablation zone 818d' bordered by a fifth proximal thermocouple 816e' at 3.5 cm. In some embodiments, the probe may include the fifth proximal thermocouple 816e' at 3.5 cm and not include the fourth proximal thermocouple 816e at 4 cm. In some embodiments, the probe may include the fourth proximal thermocouple 816e at 4 cm and not include the fifth proximal thermocouple 816e' at 3.5 cm. In some embodiments, the probe may include the fifth proximal thermocouple 816e' at 3.5 cm and the fourth proximal thermocouple 816e at 4 cm.

The probe A interface 810 also includes a generator wattage section 820, a timer 822, and an impedance section 826. The generator wattage section 820 shows the current power output of the generator. The timer 822 shows the time elapsed during an ablation procedure. A timer reset button 824 may be used to reset the timer 822. The impedance section 826 displays the current impedance measurement of the tissue surrounding the probe.

In the illustrated embodiment, the tumor ablation generator is only coupled to one probe via the first port. Because of this, the probe A interface 810 is enabled while the probe B interface 830 is disabled. In the illustrated embodiment, the interface 800 indicates that the probe B interface 830 is disabled by graying out probe B interface 830 and making elements of the probe B interface 830 non-interactive. In some embodiments, the interface 800 hides a subinterface that is disabled. These disabled cues may visually indicate to a user that no probe is coupled to the second port, or if a probe is connected to the second port, that the probe is malfunctioning. The probe B interface 830 includes the same elements as the probe A interface 810. The probe B interface 830 may be used to control and monitor a second probe as described with reference to the probe controlled and monitored by the probe A interface 810.

Figure 9:
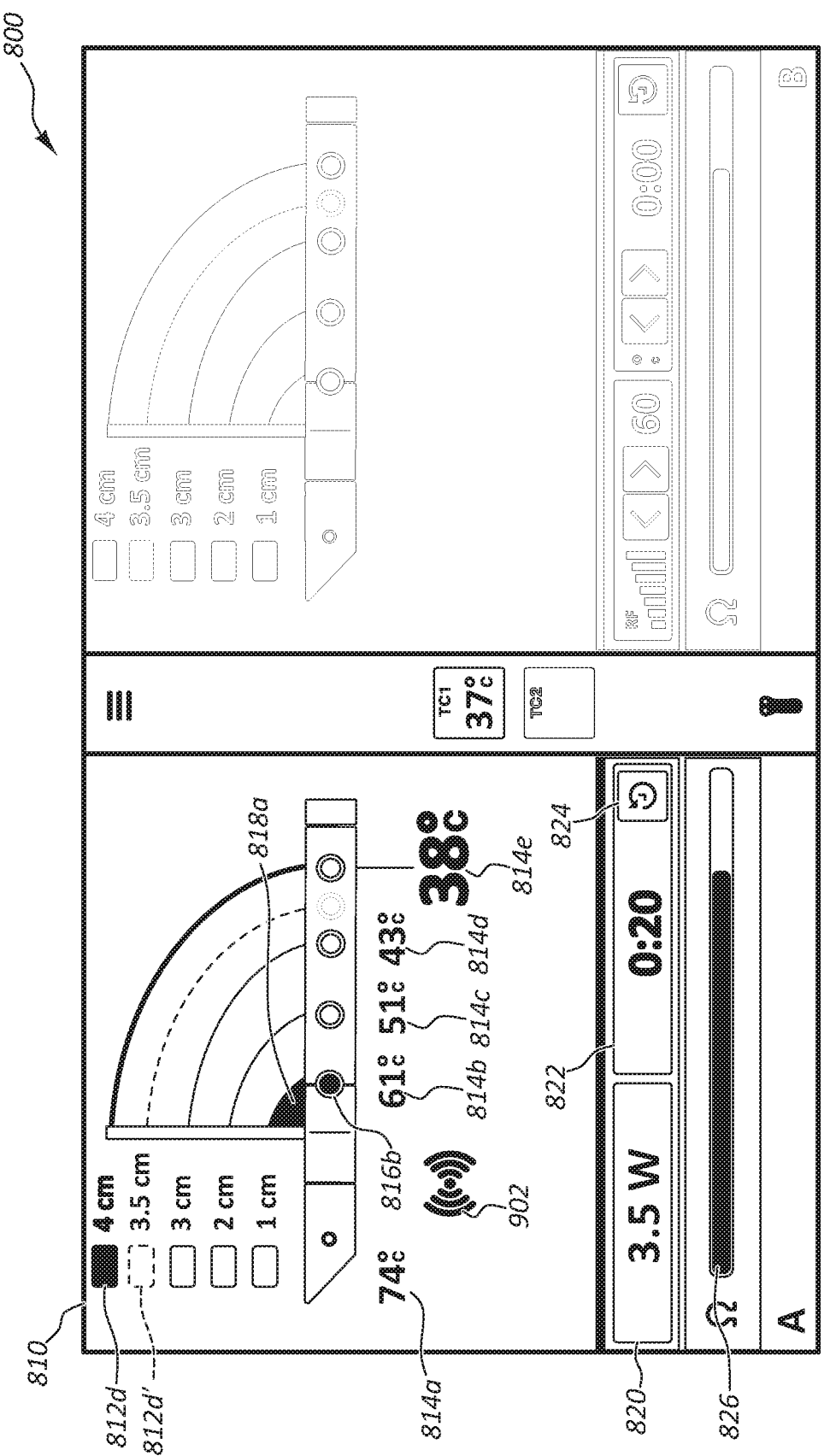
FIG. 9 illustrates the interface of FIG. 8 at a first instance of a tumor ablation procedure.

FIG. 9 illustrates the interface 800 of FIG. 8 at a first instance of a tumor ablation procedure. The timer 822 indicates that the tumor ablation procedure has been in progress for 20 seconds. As shown, the probe A interface 810 provides feedback to the user concerning the current conditions of the ablation zone, the probe, and the generator power output.

For this example, the user has selected the fourth zone input 812d. The interface 800 indicates the selection by filling in the fourth zone input 812d. In some embodiments, the interface 800 may fill the selected zone input in with a different color, highlight the selected zone input, and/or indicate the selected zone input using a heavier line representing the ablation zone.

The interface 800 may indicate that power is being sent from the generator to the probe. For example, the interface 800 may include an RF symbol 902 to indicate that the probe is radiating. The interface 800 in the illustrated embodiment includes the generator wattage section 820 to display the current power output of the generator. As shown, during the first instance of a tumor ablation procedure, the power may be 3.5 watts.

The impedance section 826 indicates the impedance of the tissue between the conductors of the probe. In the illustrated embodiment, the impedance remains the same as it was before the tumor ablation procedure, as shown in FIG. 8. If the impedance is increased, the tumor ablation procedure may become less effective. The impedance increasing is an indication that tissue charring has occurred, which reduces the efficacy of the RF transmission between the conductors of the probe. To limit the increase of impedance, in some embodiments, the generator reduces the power output if the impedance increases and/or if the maximum distal temperature is reached.

In the illustrated first instance of a tumor ablation procedure, the thermocouples 816 indicate temperature measurements 814 of the tissue after 20 seconds. Specifically, at 20 seconds the first proximal thermocouple 816b has exceeded 60° C. In some embodiments when 60° C. is reached, the tissue has been determined killed. In some embodiments, the system may consider the thermal dose (time and temperature function) received by the tissue to determine when the tissue is killed. The interface 800 indicates the area of the ablated or dead tissue by shading the first ablation zone 818a.

Figure 10:
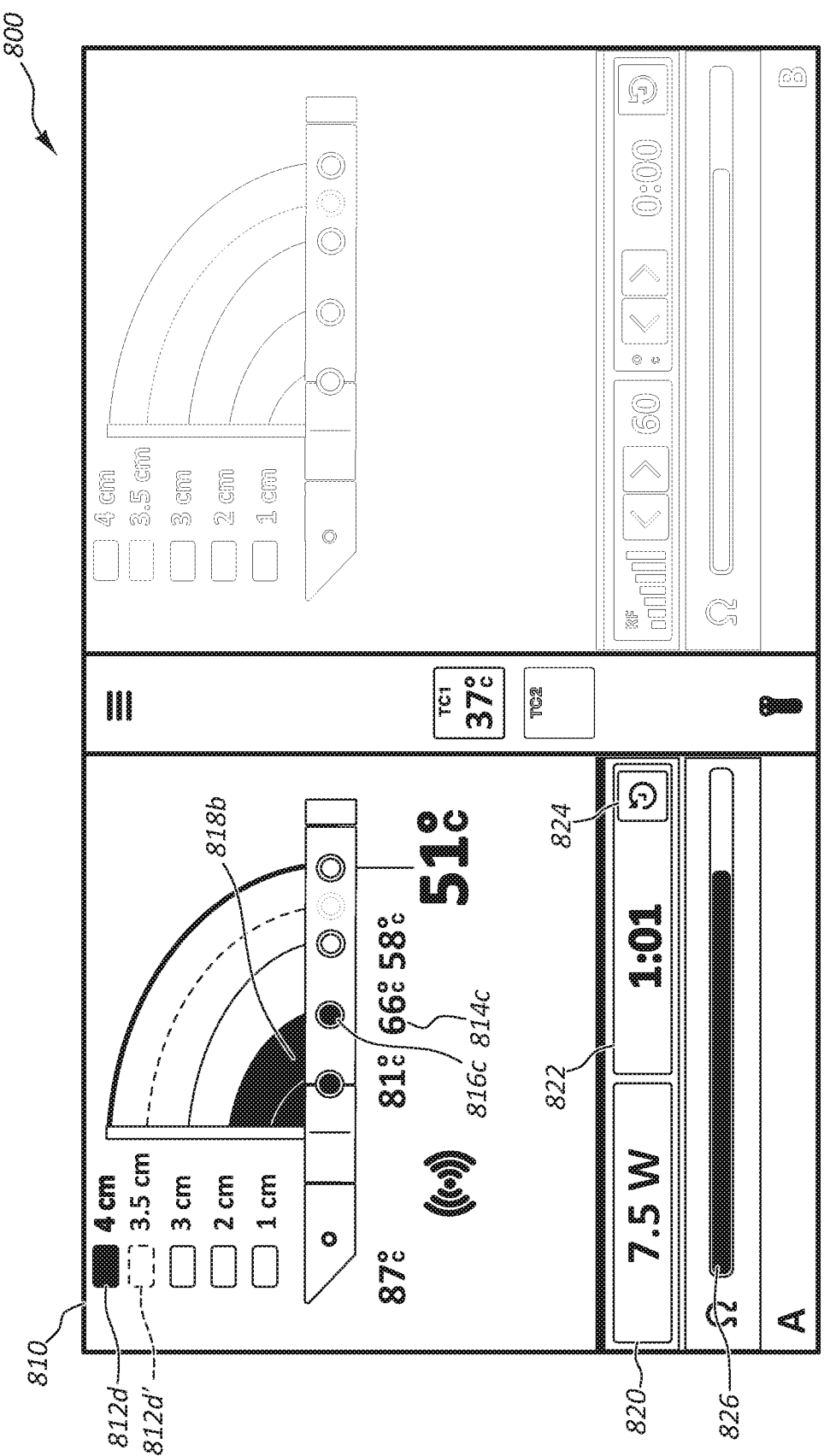
FIG. 10 illustrates the interface of FIG. 8 at a second instance of a tumor ablation procedure.

FIG. 10 illustrates the interface 800 of FIG. 8 at a second instance of a tumor ablation procedure. The timer 822 indicates that the tumor ablation procedure has been in progress for one minute and one second. As shown, the probe A interface 810 provides feedback to the user concerning the current conditions of the ablation zone, the probe, and the generator power output.

As shown, in this example the impedance section 826 has not increased between 20 seconds (FIG. 9) and a minute one second (FIG. 10). In some embodiments, because the impedance has not increased, the generator may increase power output. In some embodiments, the power can be increased while the distal thermocouple measures a temperature below a maximum temperature setpoint. In some embodiments, the maximum temperature setpoint may be 90° C. Thus, in some embodiments, power may be increased as long as the distal thermocouple measures a temperature below a reference temperature, such as 90° C. In some embodiments, the generator may increase the power output based on a combination of impedance measurements and distal thermocouple temperature measurements. For example, power may be increased if the impedance and the temperature are below a maximum threshold. As shown in the generator wattage section 820, in this example the power output has been increased to 7.5 watts. The additional power output by the generator can result in faster tumor ablation.

In the illustrated second instance of a tumor ablation procedure (FIG. 10), the thermocouples 816 indicate temperature measurements 814 of the tissue after one minute and one second. Specifically, the second proximal thermocouple 816c has exceeded 60° C. The interface 800 indicates the tissue within the second ablation zone 818b is ablated or dead by shading the second ablation zone 818b.

Figure 11:
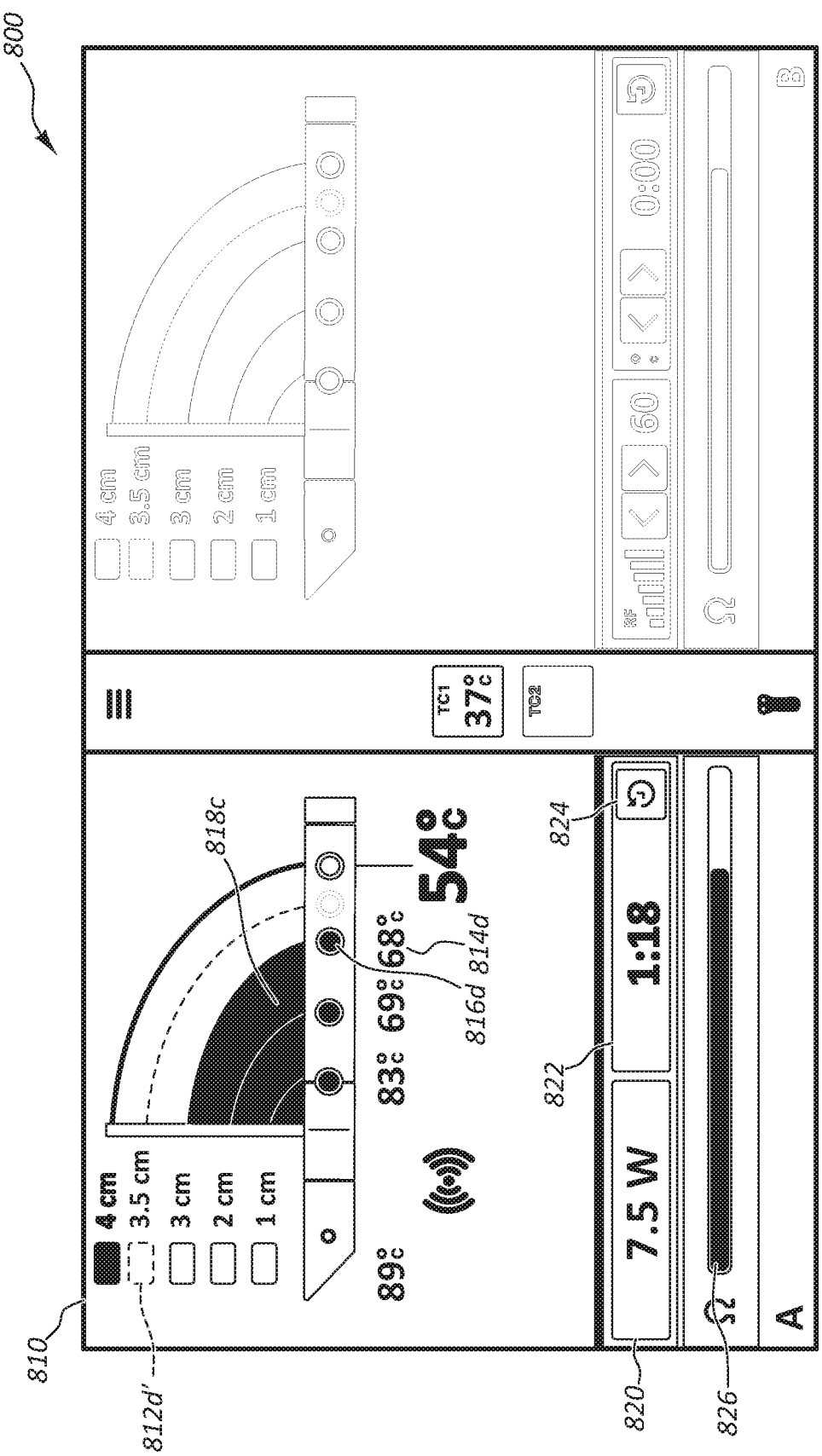
FIG. 11 illustrates the interface of FIG. 8 at a third instance of a tumor ablation procedure.

FIG. 11 illustrates the interface 800 of FIG. 8 at a third instance of a tumor ablation procedure. The timer 822 indicates that the tumor ablation procedure has been in progress for one minute and eighteen seconds. The probe A interface 810 provides feedback to the user concerning the current conditions of the ablation zone, the probe, and the generator power output.

In this example the impedance section 826 has not increased between a minute one second (FIG. 10) and one minute and eighteen seconds (FIG. 11). Because the impedance has not increased, the generator may increase power output. However, the power output by the generator may be limited by the generator or based on user settings.

As shown in the generator wattage section 820, in this example the power output has remained at 7.5 watts.

In the illustrated third instance of a tumor ablation procedure (FIG. 11), the thermocouples 816 indicate temperature measurements 814 of the tissue after one minute and eighteen seconds. Specifically, the third proximal thermocouple 816d area gets filled when the temperature at the third proximal thermocouple 816d reaches a target value during which cell death is set to occur (e.g., exceeding 60° C. for a predetermined amount of time). The interface 800 indicates the tissue within the third ablation zone 818c is ablated or dead by shading the third ablation zone 818c.

Figure 12:
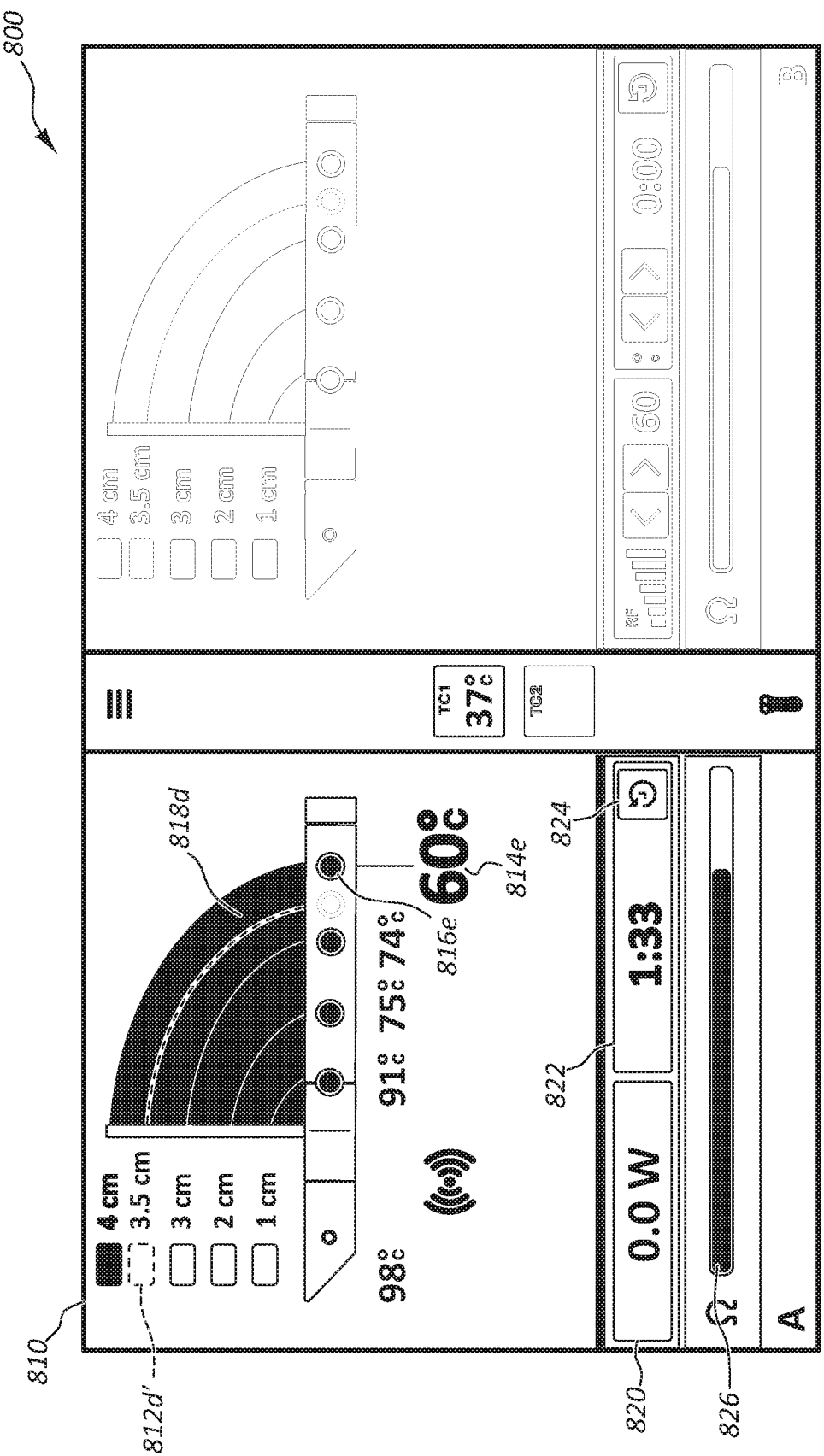
FIG. 12 illustrates the interface of FIG. 8 at a fourth instance of a tumor ablation procedure.

FIG. 12 illustrates the interface 800 of FIG. 8 at a fourth instance of a tumor ablation procedure. The timer 822 indicates that the tumor ablation procedure has been in progress for one minute and thirty-three seconds. The probe A interface 810 provides feedback to the user concerning the current conditions of the ablation zone, the probe, and the generator power output.

In the illustrated fourth instance of a tumor ablation procedure, the thermocouples 816 indicate temperature measurements 814 of the tissue after one minute and thirty-three seconds. Specifically, the fourth proximal thermocouple 816e has exceeded 60° C. The interface 800 indicates the tissue within the fourth ablation zone 818d is ablated or dead by shading the second ablation zone 818d.

At this point in the procedure, the ablation zone has reached the limit set by the user (4 cm). As shown, the generator stops providing power once the thermocouple at the edge of the desired ablation zone has reached 60° C. for a certain amount of time. In some embodiments, the generator stops providing power once the thermocouple at the edge of the desired ablation zone has received a target thermal dose which the system may determine using time at a temperature. In some such embodiments, the generator may stop before 60° C.

Figure 13:
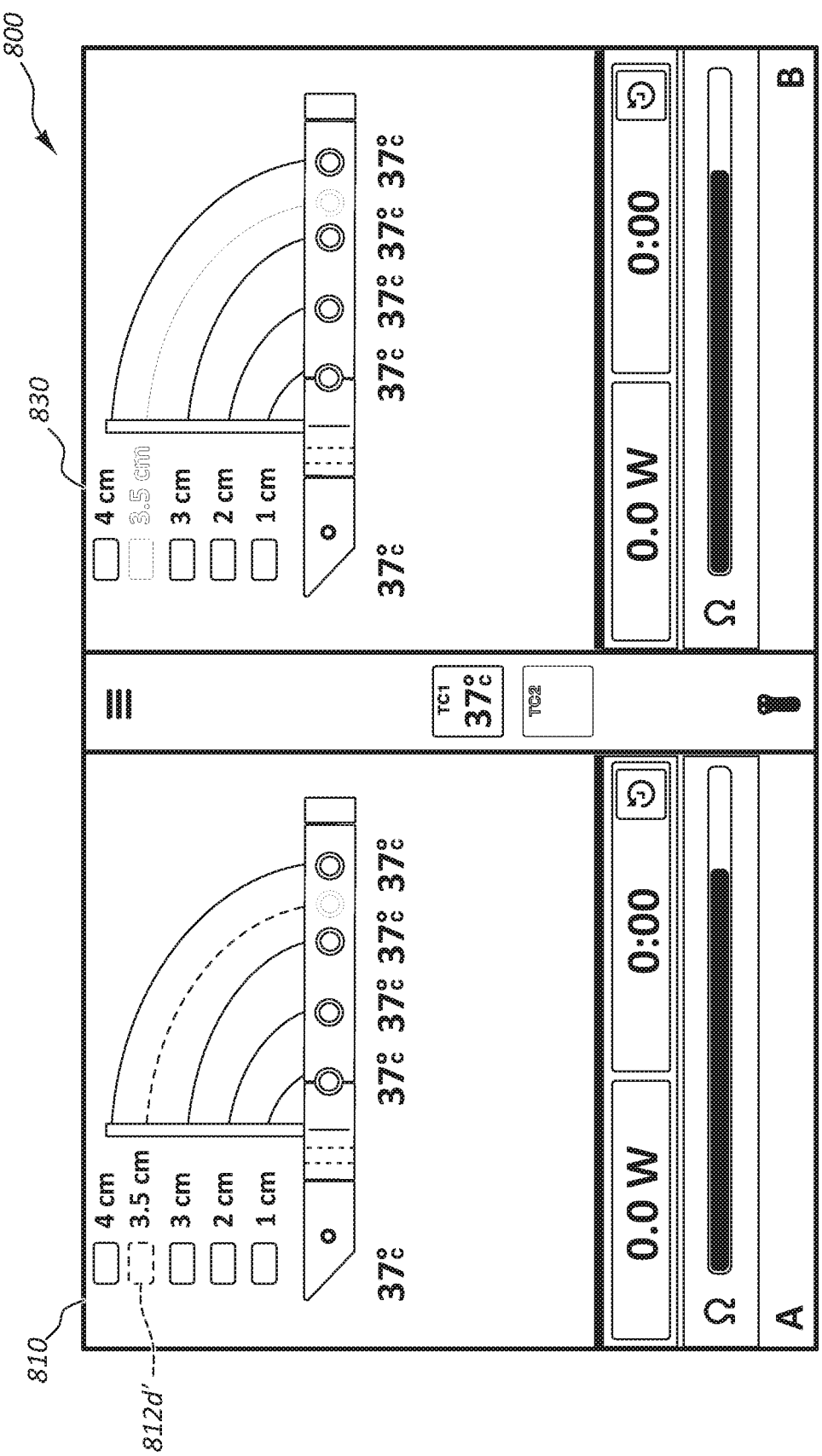
FIG. 13 illustrates the interface of FIG. 8 with the generator coupled to two probes.

FIG. 13 illustrates the interface 800 of FIG. 8 with the generator coupled to two probes. As shown, both the probe A interface 810 and the probe B interface 830 are functional and neither is grayed out. In some embodiments, the generator may detect capabilities or configuration of the probe and adapt the interface 800 accordingly. For example, if a probe had only a single thermocouple, the representation on the interface 800 would only comprise one thermocouple. As another example, in some embodiments, the generator may detect how far the conductors are extended from one another when the probe is extendable and alter distances associated with the zone control inputs.

The two probes may operate independent of each other. For example, there may be two generators, and each probe may be powered by a separate generator. The generators may modulate power output to the individual ports independently. The user may select a different size ablation zones for each of the probes.

In some embodiments, the generator modulates power output to individual ports in a dual probe configuration. For example, a first current output associated with a first port can be decreased when the impedance measured between conductors of a first probe increases, and a second current output from a second port can be decreased when the impedance measured between conductors of a second probe increases. In some embodiments, a tumor ablation system may monitor a third impedance, where the third impedance is between the first probe and the second probe. In some embodiments, the first current output and the second current output are decreased when the third impedance increases.

Some embodiments may include indicator lights associated with the ports and/or the probes. The indicator lights may be different colors. In some embodiments, elements of the interface 800 may be shown in different colors. The indicator lights and/or elements of the display may match a color of a light on a probe coupled to the port to indicate which port the probe is connected to.

In some embodiments, the tumor ablation system may emit a tone indicating that the generators are outputting power. In embodiments where two probes are being used, two different tones may be emitted to indicate that power is being output to two probes. In some embodiments, if a first probe indicates that the desired ablation zone is reached prior to a second probe, power output to the first probe may cease and a tone associated with the first probe may stop while power output to the second probe may continue and a tone associated with the second probe may continue.

Figure 14:
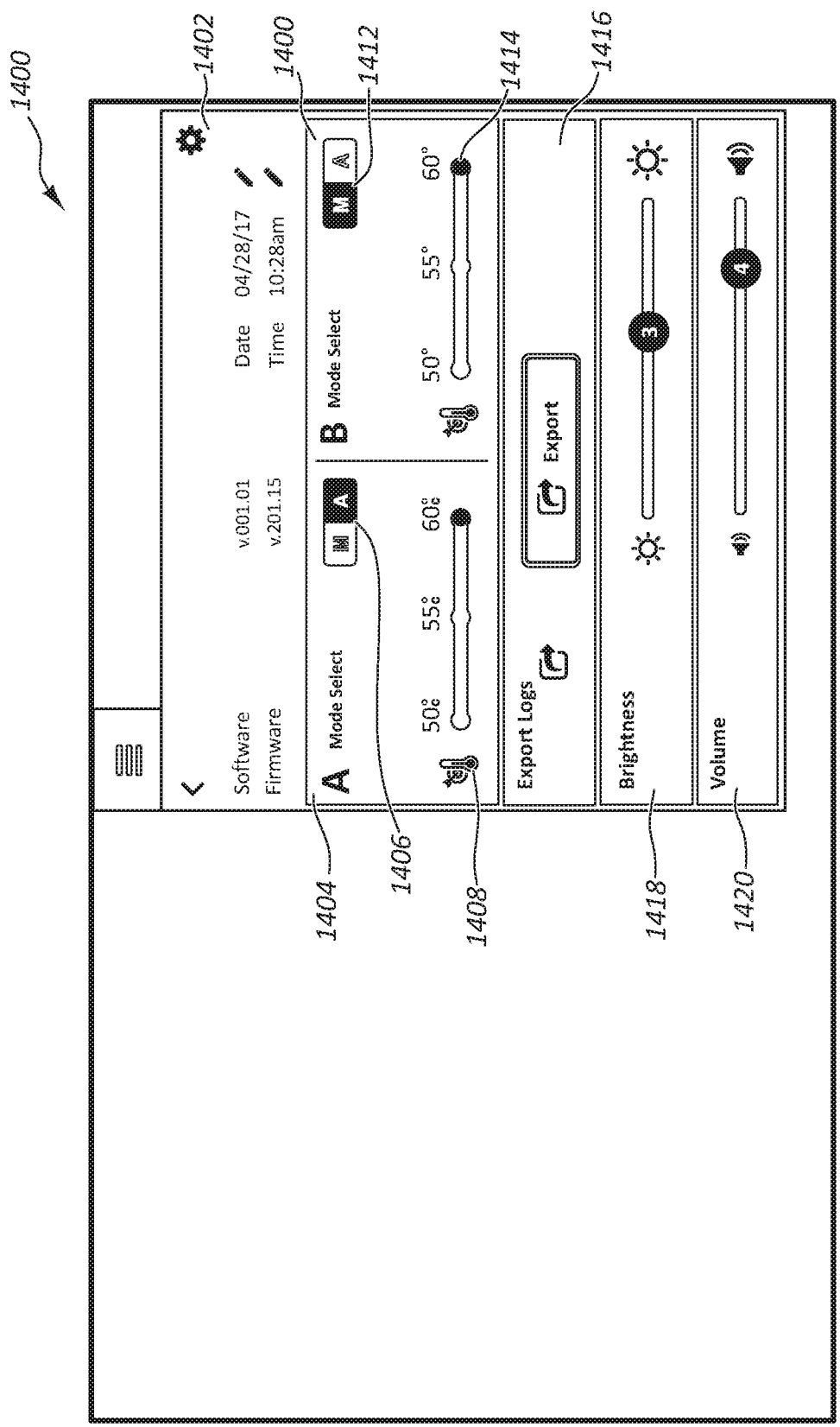
FIG. 14 illustrates a settings menu for a tumor ablation generator, according to one embodiment.

FIG. 14 illustrates a settings menu 1400 for a tumor ablation generator, according to one embodiment. As shown, the settings menu 1400 may comprise a general settings section 1402, where the user may change the date and time and view information about the generator. The settings menu 1400 may also comprise a brightness control 1418 and a volume control 1420.

In the illustrated embodiment, the settings menu 1400 includes an export logs section 1416. A user may use the export logs section 1416 to export the data from a tumor ablation procedure. The data may include but is not limited to power output by generator, duration of operation, size of ablation area, and temperature measurements. For example, the exported data may send the temperature and an amount of time at the temperature for all thermocouples. In some embodiments, the position of the probe (e.g., position within the bone and/or shape of the distal end of the probe) may also be exported. The exported data may also correlate the data to time readings so that the process of the surgery may be reviewed. In some embodiments, the exported data may be used to overlay the procedure on an image (e.g., MRI). For example, a display may illustrate the growth of the ablation zone on the image at any stage of the procedure. The overlay may be done in real-time as the surgery progresses or reviewed after the surgery. In some embodiments, the data may be used to generate a three-dimensional visualization of the ablation zone.

In some embodiments, the shape of the overlay may be affected based on the articulation of the distal end of the probe. For example, the overlay may provide a visual image of a shape of a potential ablation zone prior to a procedure based on the articulation of the distal end of the probe. In some embodiments, the potential ablation zones 818 on the interface 800 may change based on the articulation of the distal end of the probe. In some embodiments, the probes may include a piezoelectric sensor to determine the amount of articulation.

The illustrated embodiment also includes a probe A mode section 1404 and a probe B mode section 1410 (collectively mode sections). The mode sections 1404, 1410 include a toggle (i.e., first toggle 1406, second toggle 1412) that allows a user to select automatic mode or manual mode. In automatic mode, the generator adjusts power output based on temperature measurements and impedance measurements. In manual mode, the user may determine the power output. A first slider 1408 and second slider 1414 may control a target temperature for a desired thermocouple to reach before turning off RF power output.

Figure 15:
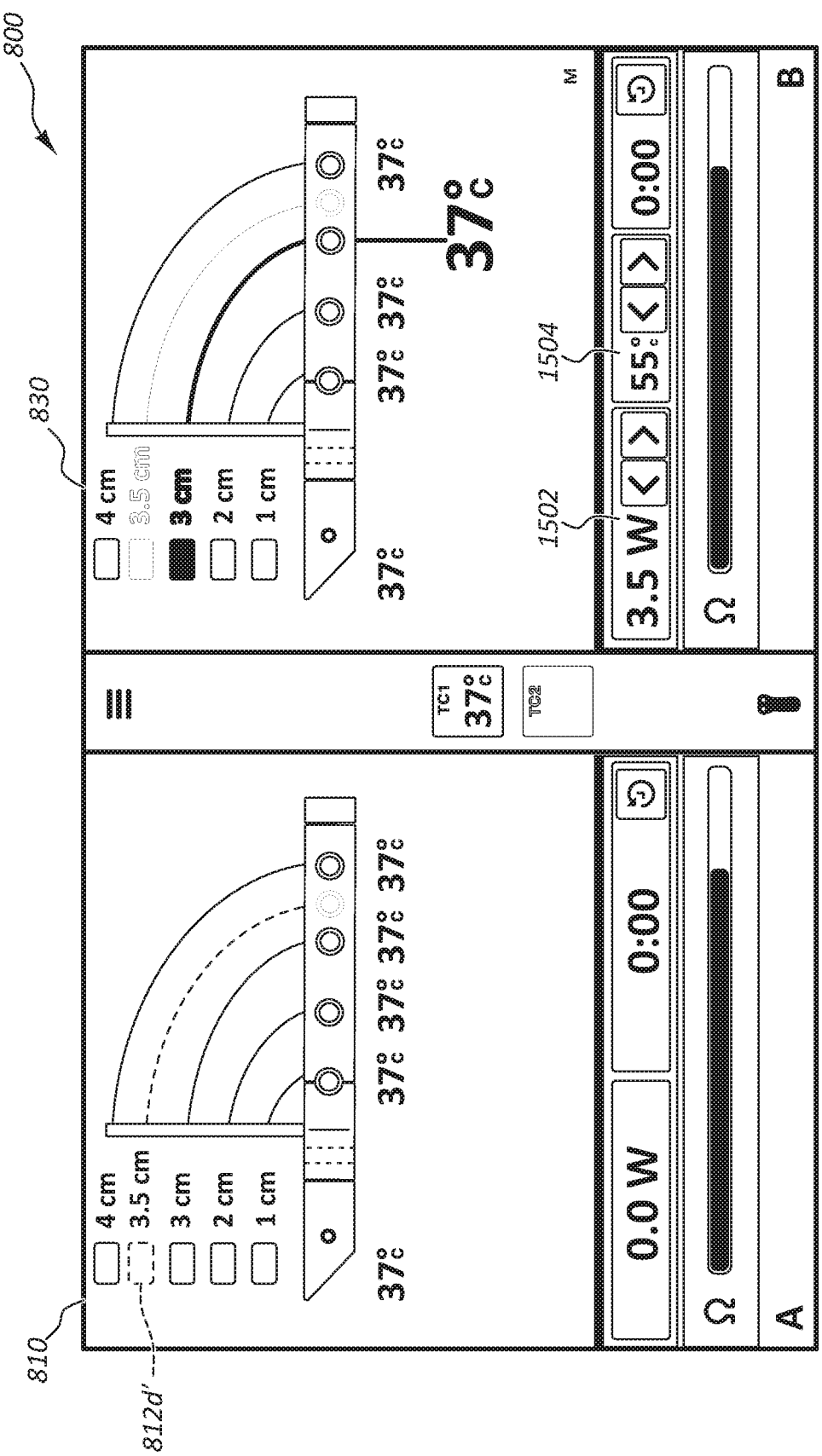
FIG. 15 illustrates the interface of FIG. 8 coupled to two probes, where the probe A interface is in automatic mode, and the probe B interface is also in operation.

FIG. 15 illustrates the interface 800 of FIG. 8 coupled to two probes, where the probe A interface 810 is in automatic mode, and the probe B interface 830 is also in operation. When in the illustrated mode, the probe B interface 830 includes an adjustable power output 1502 and an adjustable target temperature 1504 for the selected thermocouple. The user may adjust these inputs manually based on the desired procedure. For example, the user may desire that the target temperature be 85° C. for 13 seconds.

Figure 16:
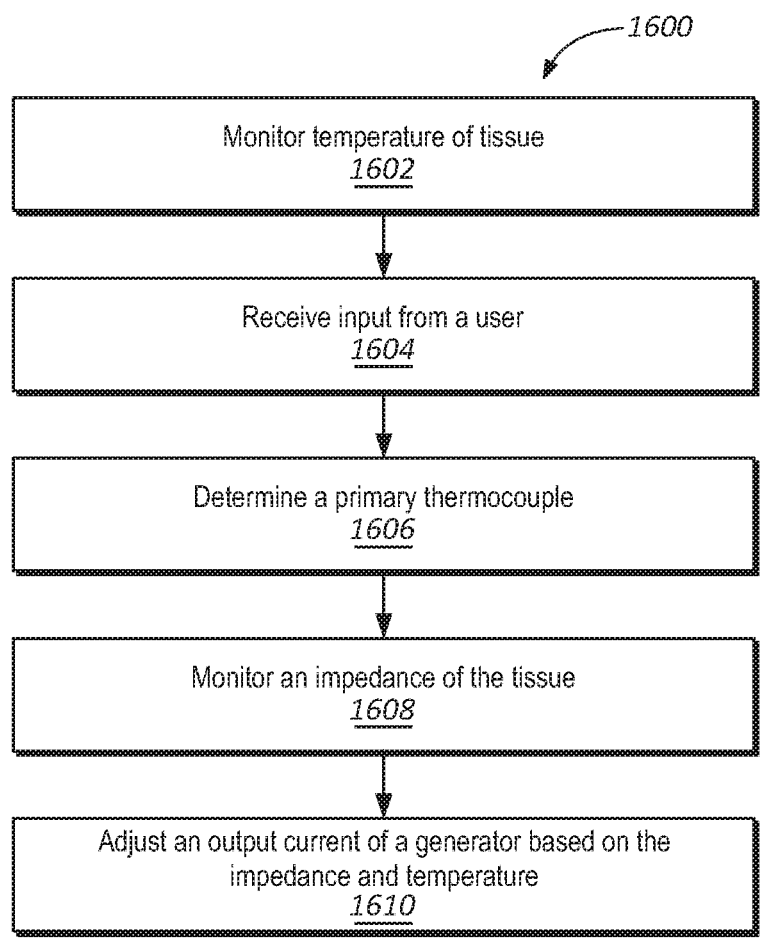
FIG. 16 illustrates a flow chart of a method for controlling a power output of a generator of a tumor ablation system based on tissue impedance and temperature.

FIG. 16 illustrates a flow chart of a method 1600 for controlling a power output of a generator of a tumor ablation system based on tissue impedance. A tumor ablation system monitors 1602 temperature of tissue surrounding a probe via multiple thermocouples. The multiple thermocouples measure temperature at different points along a length of the probe. The tumor ablation system receives 1604 input from a user indicating a desired ablation region. The tumor ablation system determines 1606 a primary thermocouple by determining which of the multiple thermocouples is nearest an outer perimeter of the desired ablation region. The tumor ablation system monitors 1608 an impedance of the tissue between a first conductor and a second conductor of the probe. The tumor ablation system adjusts 1610 an output current of a generator based on the measured impedance and temperature. The generator produces an electrical alternating current to be conducted between the first conductor and the second conductor via tissue within the desired ablation region. In one embodiment, the tumor ablation system decreases the output power when the impedance increases and/or when a maximum distal temperature is reached, and stops the output current when a temperature or thermal energy measurement at the primary thermocouple reaches a target threshold.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to an "embodiment" means that a particular feature, structure, or characteristic described in connection with that embodiment is included in at least one embodiment. Thus, references to embodiments throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. A system for tumor ablation, the system comprising:
    a probe comprising:
        a first conductor;
        a second conductor disposed distal to the first conductor;
        an insulator bushing disposed between the first conductor and the second conductor; and
        a first thermocouple to measure a temperature at a location on the second conductor;
        a second thermocouple on the second conductor;
        a third thermocouple on the second conductor; and
        a fourth thermocouple on the second conductor;
    a generator to produce a current to be conducted between the first conductor and the second conductor to create an ablation region with a first potential ablation perimeter, and wherein the second thermocouple, the third thermocouple, and the fourth thermocouple respectively define a second point along a second potential ablation perimeter, a third point along a third potential ablation perimeter, and a fourth point along a fourth potential ablation perimeter, wherein each of the potential ablation perimeters is different;
    a display; and
    a processor to:
        monitor the temperature at the first thermocouple;
        monitor an impedance of the tissue between the first conductor and the second conductor;
        control an output of the generator to decrease the current when the impedance increases and to stop the current when a thermal dose reaches a target threshold;
        control the output of the generator based on a type of a procedure being performed; and
        configure the display to provide a graphical user interface illustrating the first potential ablation perimeter, the second potential ablation perimeter, the third potential ablation perimeter, and the fourth potential ablation perimeter.

2. The system of claim 1, wherein the graphical user interface receives size input from a user to specify which of the first potential ablation perimeter, the second potential ablation perimeter, the third potential ablation perimeter, and the fourth potential ablation perimeter is to be used to define the desired ablation region.

3. The system of claim 2, wherein the display comprises a touchscreen, and wherein the size input is received via the touchscreen.

4. The system of claim 1, wherein the graphical user interface superimposes one or more of the potential ablation perimeters on an image of the tissue.

5. The system of claim 1, further comprising a fifth thermocouple on the first conductor.

6. The system of claim 5, wherein the processor is further to control the generator based on temperature measurements of the first thermocouple and the fifth thermocouple.

7. The system of claim 1, wherein the processor is further to receive manual ablation input from a user to selectively override impedance-based control of the generator, wherein the manual ablation input specifies a time period to apply a target power level.

8. The system of claim 1, further comprising a display to provide a graphical user interface illustrating a mode selection that allows a user to switch between an automatic mode and a manual mode, wherein:
    in the automatic mode, the generator is configured to automatically adjust the output of the generator based on one or more of the temperature at the first thermocouple or the impedance of the tissue, and
    in the manual mode, the user determines the output of the generator.

9. A non-transitory computer-readable medium including instructions, that when executed by one or more processors of a tumor ablation system, cause the tumor ablation system to:
    monitor temperature of tissue surrounding a probe via multiple thermocouples, the multiple thermocouples to measure temperature at different points along a length of the probe;
    configure a display to provide a graphical user interface illustrating a first potential ablation zone, a second potential ablation zone, a third potential ablation zone, and a fourth potential ablation zone, wherein each of the potential ablation zones corresponds to one of the multiple thermocouples;
    receive input from a user indicating a desired ablation region corresponding to one of the potential ablation zones;
    determine a primary thermocouple by determining which of the multiple thermocouples is nearest an outer perimeter of the desired ablation region;
    monitor an impedance of the tissue between a first conductor and a second conductor of the probe; and
    adjust an output current of a generator, wherein the generator produces an electrical alternating current to be conducted between the first conductor and the second conductor via tissue within the desired ablation region, the output current to:
        decrease when the impedance increases,
        decrease when a maximum distal temperature is reached, and
        stop when a thermal dose at the primary thermocouple reaches a target threshold, be based on a type of a procedure being performed, and
        be based on a type of a procedure being performed.

10. The non-transitory computer-readable medium of claim 9, wherein the instructions, when executed by the one or more processors, further cause the tumor ablation system to monitor a temperature at a distal portion of the probe via a distal thermocouple, wherein the output current is adjusted based on the temperature at the distal portion.

11. The non-transitory computer-readable medium of claim 9, wherein the instructions, when executed by the one or more processors, further cause the tumor ablation system to superimpose the desired ablation region on an image of a tumor displayed in the graphical user interface.

12. The non-transitory computer-readable medium of claim 11, wherein the image is a magnetic resonance imaging scan.

13. The non-transitory computer-readable medium of claim 9, wherein adjusting the output current of the generator is based on user-defined parameters.

14. A system for tumor ablation, the system comprising:
a first probe comprising:
- a first set of thermocouples to measure temperature at different points along the first probe, and
- a first conductor and a second conductor;

a second probe comprising:
- a second set of thermocouples to measure temperature at different points along the second probe, and
- a third conductor and a fourth conductor;

a generator to provide a first current output to the first probe and a second current output to the second probe; and a processor to:
- monitor temperature measurements from the first set of thermocouples and the second set of thermocouples;
- monitor a first impedance between the first conductor and the second conductor, and a second impedance between the third conductor and the fourth conductor;
- monitor a third impedance between the first conductor and the third conductor; and
- adjust the first current output and the second current output of the generator based on the first impedance, the second impedance, the third impedance, the temperature measurements, and a type of a procedure being performed.

15. The system of claim 14, wherein the first current output is decreased when the first impedance increases, and the second current output is decreased when the second impedance increases.

16. The system of claim 14, wherein the first current output is decreased when the first impedance increases and when the second impedance increases.

17. The system of claim 14, wherein the first current output and the second current output are decreased when the third impedance increases.

18. The system of claim 14, wherein:
the generator comprises:
- a first port and a second port to couple with the first probe and the second probe, and
- a first indicator light associated with the first port, and a second indicator light associated with the second port;

the first probe further comprises a third indicator light; and the second probe further comprises a fourth indicator light, wherein the processor is further to:
- cause a color of the third indicator light to match the first indicator light when the first probe is coupled to the first port,
- cause the color of the third indicator light to match the second indicator light when the first probe is coupled to the second port,
- cause a color of the fourth indicator light to match the first indicator light when the second probe is coupled to the first port, and
- cause the color of the fourth indicator light to match the second indicator light when the second probe is coupled to the second port.

* * * * *